(12) United States Patent
Hagemann

(10) Patent No.: US 10,047,164 B2
(45) Date of Patent: Aug. 14, 2018

(54) METHODS AND COMPOSITIONS FOR THE TREATMENT OF PANCREATIC CANCER

(71) Applicant: Opsona Therapeutics Ltd., Dublin (IE)

(72) Inventor: Thorsten Hagemann, London (GB)

(73) Assignee: OPSONA THERAPEUTICS LIMITED, Dublin (IE)

( * ) Notice: Subject to any disclaimer, the term of this patent is extended or adjusted under 35 U.S.C. 154(b) by 0 days.

(21) Appl. No.: 15/244,833

(22) Filed: Aug. 23, 2016

(65) Prior Publication Data

US 2016/0355603 A1 Dec. 8, 2016

Related U.S. Application Data

(63) Continuation-in-part of application No. 14/429,278, filed as application No. PCT/EP2013/007041 on Oct. 1, 2013, now abandoned.

(30) Foreign Application Priority Data

Oct. 19, 2012 (EP) .................................. 12189212

(51) Int. Cl.

| C07K 16/28 | (2006.01) |
|---|---|
| A61K 39/395 | (2006.01) |
| A61K 31/7068 | (2006.01) |
| A61K 31/337 | (2006.01) |
| A61K 45/06 | (2006.01) |
| G01N 33/574 | (2006.01) |
| G01N 33/50 | (2006.01) |
| C07K 14/705 | (2006.01) |
| A61K 39/00 | (2006.01) |

(52) U.S. Cl.
CPC ........ *C07K 16/2896* (2013.01); *A61K 31/337* (2013.01); *A61K 31/7068* (2013.01); *A61K 39/3955* (2013.01); *A61K 45/06* (2013.01); *G01N 33/5011* (2013.01); *G01N 33/57438* (2013.01); *A61K 2039/505* (2013.01); *A61K 2039/54* (2013.01); *A61K 2039/545* (2013.01); *C07K 2317/24* (2013.01); *C07K 2317/34* (2013.01); *C07K 2317/56* (2013.01); *C07K 2317/565* (2013.01); *C07K 2317/76* (2013.01); *G01N 2500/04* (2013.01)

(58) Field of Classification Search
CPC .. A61K 2039/505; A61K 38/00; A61K 38/08; A61K 38/1709; A61K 39/395; A61K 39/3955; A61K 38/10; A61K 38/17; C07K 2317/76; C07K 2319/00; C07K 16/18; C07K 16/2896; C07K 2317/56; C07K 14/435; C07K 7/06; C07K 7/08; C07K 14/47; C07K 14/70596; C07K 16/28; C07K 14/705
See application file for complete search history.

(56) References Cited

U.S. PATENT DOCUMENTS

2009/0217401 A1* 8/2009 Korman ............. C07K 16/2818
800/18

FOREIGN PATENT DOCUMENTS

| WO | WO-2005/028509 A1 | 3/2005 |
|---|---|---|
| WO | WO-2006/077471 A2 | 7/2006 |
| WO | WO-2008/132516 A1 | 11/2008 |
| WO | WO-2011/003925 A1 | 1/2011 |

OTHER PUBLICATIONS

Bork, A. Powers and pitfalls in sequence analysis: the 70% hurdle. Genome Res 10: 398-400, 2000.*
Bork et al. Go hunting in sequence databases but watch out for the traps. Trends in Genetics. 12(10): 425-427, 1996.*
Brenner, S.E. Errors in genome function. Trends in Genetics 15(4): 132-133, 1999.*
Brorson et al. Mutational analysis of avidity and fine specificity of anti-levan antibodies. J Immunol 163: 6694-6701, 1999.*
Brummell et al. (Biochemistry 32:1180-1187 (1993)).*
Burks et al. (PNAS 94:412-417 (1997)).*
Colman, P.M. Research in Immunol. 145:33-36 (1994).*
Doerks et al. Protein annotation: detective work for function prediction. Trends in Genetics 14(6): 248-250, 1998.*
Jang et al. (Molec. Immunol. 35:1207-1217 (1998)).*
Kobayashi et al. (Protein Engineering 12:879-844 (1999)).*
Miele et al. Albumin-bound formulation of paclitaxel (Abraxane ABI-007) in the treatment of breast cancer. Int J Nanomed 4: 99-105, 2009.*
Ngo et al. Computational complexity, protein structure prediction, and the Levinthal paradox. The Protein Folding Problem and Tertiary Structure Prediction, pp. 492-495, 1994.*
Skolnick et al. From genes to protein structure and function: novel applications of computational approaches in the genomic era. Trends in Biotech 18(1): 34-39, 2000.*
Smith et al. The challenges of genome sequence annotation or "The devil is in the details". Nature Biotech 15: 1222-1223, 1997.*
Tokuriki et al. Stability effects of mutations and protein evolvability. Curr Opin Structural Biol 19: 596-604, 2009.*
Von Hoff et al. Gemcitabine plus nab-paclitaxel is an active regimen in patients with advanced pancreatic cancer: a phase I/II trial. J Clin Oncol 29(34): 4548-4554, 2011.*
Wells. J.A. Additivity of mutational effects in proteins. Biochemistry 29 (37): 8509-8517, 1990.*

(Continued)

*Primary Examiner* — Bridget E Bunner
(74) *Attorney, Agent, or Firm* — Marshall, Gerstein & Borun LLP

(57) ABSTRACT

A composition comprising a TLR2 antagonistic antibody or antigen binding fragment thereof for use in the treatment or prophylaxis of pancreatic cancer is provided. The antibody or antigen binding fragment may be provided for simultaneous, separate or sequential administration with a secondary chemotherapeutic agent such as gemcitabine, and optionally a tertiary chemotherapeutic agent such as abraxane for enhanced treatment. Also provided is a screening method for the identification of compounds for use in treatment or prevention of pancreatic cancer.

18 Claims, 24 Drawing Sheets

(56) References Cited

OTHER PUBLICATIONS

Welschof, M. "Opsona Partnering Opportunity Worldwide", R&D Focus Drug News, Apr. 18, 2012.*
Garay et al., Cancer relapse under chemotherapy: Why TLR2/4 receptor agonists can help, Eur. J. Pharmacol., 563(1-3):1-17 (2007).
International Search Report and Written Opinion, International Application No. PCT/EP2013/070410, dated Nov. 19, 2013.
O'Neill et al., Therapeutic targeting of toll-like receptors for infectious and inflammatory diseases and cancer, Pharmacological Rev., 61(2):177-97 (2009).
Schwartz et al., Phenylmethimazole decreases Toll-like receptor 3 and noncanonical Wnt5a expression in pancreatic cancer and melanoma together with tumor cell growth and migration, Clin. Cancer Res., 15(12):4114-22 (2009).
Opsona Therapeutics, Poster presentation—BIO Europe Spring, Mar. 19-21, 2012 (16 pages).

\* cited by examiner

| Days | Vehicle | Gem+Abr | OPN-305 | Gem+Abr+OPN-305 | Gem+Abr→Combination | OPN-305→combination |
|---|---|---|---|---|---|---|
| 0. | 100.0 | 100.0 | 100.0 | 100.0 | 100.0 | 100.0 |
| 33. | | | | | 93.33334 | |
| 34. | | 92.30769 | | | | |
| 35. | 50.0 | | 81.81818 | | | 70.0 |
| 37. | | 76.92308 | 72.72727 | | | 60.0 |
| 38. | | | | | 78.97436 | |
| 39. | | 69.23077 | | | | |
| 40. | 25.0 | | | | | |
| 42. | 0.0 | 38.46154 | 54.54546 | 100.0 | 78.97436 | 50.0 |
| 44. | | | | 87.5 | 52.64957 | |
| 45. | | | | 75.0 | | |
| 48. | | 30.76923 | | | | |
| 49. | | 7.692307 | 0.0 | 37.5 | 26.32479 | 20.0 |
| 56. | | | | 25.0 | 13.16239 | 0.0 |
| 57. | | | | | 0.0 | |
| 63. | | | | 0.0 | | |

Figure 4(b)

Comparison of Survival Curves

Log-rank (Mantel-Cox) test (recommended)

| | |
|---|---|
| Chi square | 28.39 |
| df | 5 |
| P value | < 0.0001 |
| P value summary | **** |
| Are the survival curves sig different? | Yes |

Logrank test for trend (recommended)

| | |
|---|---|
| Chi square | 8.648 |
| df | 1 |
| P value | 0.0033 |
| P value summary | ** |
| Sig. trend? | Yes |

Figure 4(c)

Survival Proportions

| Days | Vehicle | Gem+Abr | OPN-305 | Gem+Abr+OPN-305 |
|---|---|---|---|---|
| 0. | 100.0 | 100.0 | 100.0 | 100.0 |
| 34. |  | 92.30769 |  |  |
| 35. | 50.0 |  | 81.81818 |  |
| 37. |  | 76.92308 | 72.72727 |  |
| 39. |  | 69.23077 |  |  |
| 40. | 25.0 |  |  |  |
| 42. | 0.0 | 38.46154 | 54.54546 | 100.0 |
| 44. |  |  |  | 87.5 |
| 45. |  |  |  | 75.0 |
| 48. |  | 30.76923 |  |  |
| 49. |  | 7.692307 | 0.0 | 37.5 |
| 56. |  | 0.0 |  | 25.0 |
| 63. |  |  |  | 0.0 |

Figure 5(b)

Comparison of Survival Curves

Log-rank (Mantel-Cox) test (recommended)

| | |
|---|---|
| Chi square | 26.74 |
| df | 3 |
| P value | < 0.0001 |
| P value summary | **** |
| Are the survival curves sig different? | Yes |

Logrank test for trend (recommended)

| | |
|---|---|
| Chi square | 22.82 |
| df | 1 |
| P value | < 0.0001 |
| P value summary | **** |
| Sig. trend? | Yes |

Figure 5(c)

Survival Proportions

| Days | Gem+Abr | Gem+Abr+OPN-305 |
|---|---|---|
| 0. | 100.000 | 100.000 |
| 34. | 92.30769 | |
| 37. | 76.92308 | |
| 39. | 69.23077 | |
| 42. | 38.46154 | 100.000 |
| 44. | | 87.500 |
| 45. | | 75.000 |
| 48. | 30.76923 | |
| 49. | 7.692307 | 37.500 |
| 56. | 0.000 | 25.000 |
| 63. | | 0.000 |

Figure 6(b)

Comparison of Survival Curves

Log-rank (Mantel-Cox) test

| | |
|---|---|
| Chi square | 9.204 |
| df | 1 |
| P value | 0.0024 |
| P value summary | ** |
| Are the survival curves sig different? | Yes |

Gehan-Breslow-Wilcoxon test

| | |
|---|---|
| Chi square | 11.53 |
| df | 1 |
| P value | 0.0007 |
| P value summary | *** |
| Are the survival curves sig different? | Yes |

Figure 6(c)

```
LRR11|human    DPGKVETLTIRRL I  F LFYDLSTLYS  333
     |mouse    ELGKVETVTIRRL I  F LFYDLSTVYS  333
     |monkey   DPGKVETVTIRRL I  F SFNDLSTLYP  333
     |pig      SLGNVETLIVRRL I  F FLFYDLRSIYS 334
              . *:***:*:*******:*: * **  ::*.

LRR12|human    LTERVKRITVENS V LVPCLLSQ     357
     |mouse    LLEKVKRITVENS V LVPCSFSQ     357
     |monkey   LTERVKRITVENS V LVPCLLSR     357
     |pig      LTGAVKRITIENS V LVPCSLSQ     358
              *   *****:********** :*:

LRR13|human    HLKSLEYLDLSEN MVE LKNSACED    384
     |mouse    HLKSLEFLDLSEN MVE LKNSACKG    384
     |monkey   HLKSLEYLDLSEN MVE LKNSACED    384
     |pig      HLKSLEYLDLSEN MSE LKNSACEH    385
              ******:******* ********:

LRR14|human    AWPSLQTLILRQN LASLEKTGETLL   410
     |mouse    AWPSLQTLVLSQN LRSMQKTGEILL   410
     |monkey   AWPSLQTLILRQN LASLGKTGETLL   410
     |pig      AWPFLHTLILRQN LKSLEKTGEVLV   411
              *** *:**:* **** *: **** *:
```

▨ Presumed antibody interaction
▨ Dimerization with TLR1 / TLR6

Figure 11

SEQUENCE LISTING

```
<160> NUMBER OF SEQ ID NOS: 15

<210> SEQ ID NO 1
<211> LENGTH: 784
<212> TYPE: PRT
<213> ORGANISM: Homo sapiens

<400> SEQUENCE: 1

Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
    50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
    130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
```

```
                195                 200                 205
        Gln His Ile Leu Leu Glu Ile Phe Val Asp Val Thr Ser Ser Val
        210                 215                 220
        Glu Cys Leu Glu Leu Arg Asp Thr Asp Leu Asp Thr Phe His Phe Ser
    225                 230                 235                 240
        Glu Leu Ser Thr Gly Glu Thr Asn Ser Leu Ile Lys Lys Phe Thr Phe
                        245                 250                 255
        Arg Asn Val Lys Ile Thr Asp Glu Ser Leu Phe Gln Val Met Lys Leu
                    260                 265                 270
        Leu Asn Gln Ile Ser Gly Leu Leu Glu Leu Glu Phe Asp Asp Cys Thr
                    275                 280                 285
        Leu Asn Gly Val Gly Asn Phe Arg Ala Ser Asp Asn Asp Arg Val Ile
        290                 295                 300
        Asp Pro Gly Lys Val Glu Thr Leu Thr Ile Arg Arg Leu His Ile Pro
        305                 310                 315                 320
        Arg Phe Tyr Leu Phe Tyr Asp Leu Ser Thr Leu Tyr Ser Leu Thr Glu
                        325                 330                 335
        Arg Val Lys Arg Ile Thr Val Glu Asn Ser Lys Val Phe Leu Val Pro
                    340                 345                 350
        Cys Leu Leu Ser Gln His Leu Lys Ser Leu Glu Tyr Leu Asp Leu Ser
                    355                 360                 365
        Glu Asn Leu Met Val Glu Glu Tyr Leu Lys Asn Ser Ala Cys Glu Asp
        370                 375                 380
        Ala Trp Pro Ser Leu Gln Thr Leu Ile Leu Arg Gln Asn His Leu Ala
    385                 390                 395                 400
        Ser Leu Glu Lys Thr Gly Glu Thr Leu Leu Thr Leu Lys Asn Leu Thr
                        405                 410                 415
        Asn Ile Asp Ile Ser Lys Asn Ser Phe His Ser Met Pro Glu Thr Cys
                    420                 425                 430
        Gln Trp Pro Glu Lys Met Lys Tyr Leu Asn Leu Ser Ser Thr Arg Ile
                    435                 440                 445
        His Ser Val Thr Gly Cys Ile Pro Lys Thr Leu Glu Ile Leu Asp Val
        450                 455                 460
        Ser Asn Asn Asn Leu Asn Leu Phe Ser Leu Asn Leu Pro Gln Leu Lys
    465                 470                 475                 480
        Glu Leu Tyr Ile Ser Arg Asn Lys Leu Met Thr Leu Pro Asp Ala Ser
                        485                 490                 495
        Leu Leu Pro Met Leu Leu Val Leu Lys Ile Ser Arg Asn Ala Ile Thr
                    500                 505                 510
        Thr Phe Ser Lys Glu Gln Leu Asp Ser Phe His Thr Leu Lys Thr Leu
                    515                 520                 525
        Glu Ala Gly Gly Asn Asn Phe Ile Cys Ser Cys Glu Phe Leu Ser Phe
        530                 535                 540
        Thr Gln Glu Gln Gln Ala Leu Ala Lys Val Leu Ile Asp Trp Pro Ala
    545                 550                 555                 560
        Asn Tyr Leu Cys Asp Ser Pro Ser His Val Arg Gly Gln Gln Val Gln
                        565                 570                 575
        Asp Val Arg Leu Ser Val Ser Glu Cys His Arg Thr Ala Leu Val Ser
                    580                 585                 590
        Gly Met Cys Cys Ala Leu Phe Leu Leu Ile Leu Leu Thr Gly Val Leu
                    595                 600                 605
        Cys His Arg Phe His Gly Leu Trp Tyr Met Lys Met Met Trp Ala Trp
        610                 615                 620
```

```
Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
            645                 650                 655

Asn Leu Met Val Gln Glu Leu Glu Asn Phe Asn Pro Pro Phe Lys Leu
        660                 665                 670

Cys Leu His Lys Arg Asp Phe Ile Pro Gly Lys Trp Ile Ile Asp Asn
    675                 680                 685

Ile Ile Asp Ser Ile Glu Lys Ser His Lys Thr Val Phe Val Leu Ser
690                 695                 700

Glu Asn Phe Val Lys Ser Glu Trp Cys Lys Tyr Glu Leu Asp Phe Ser
705                 710                 715                 720

His Phe Arg Leu Phe Glu Glu Asn Asn Asp Ala Ala Ile Leu Ile Leu
                725                 730                 735

Leu Glu Pro Ile Glu Lys Lys Ala Ile Pro Gln Arg Phe Cys Lys Leu
            740                 745                 750

Arg Lys Ile Met Asn Thr Lys Thr Tyr Leu Glu Trp Pro Met Asp Glu
        755                 760                 765

Ala Gln Arg Glu Gly Phe Trp Val Asn Leu Arg Ala Ala Ile Lys Ser
    770                 775                 780

<210> SEQ ID NO 2
<211> LENGTH: 784
<212> TYPE: PRT
<213> ORGANISM: Mus musculus

<400> SEQUENCE: 2

Met Leu Arg Ala Leu Trp Leu Phe Trp Ile Leu Val Ala Ile Thr Val
1               5                   10                  15

Leu Phe Ser Lys Arg Cys Ser Ala Gln Glu Ser Leu Ser Cys Asp Ala
            20                  25                  30

Ser Gly Val Cys Asp Gly Arg Ser Arg Ser Phe Thr Ser Ile Pro Ser
        35                  40                  45

Gly Leu Thr Ala Ala Met Lys Ser Leu Asp Leu Ser Phe Asn Lys Ile
    50                  55                  60

Thr Tyr Ile Gly His Gly Asp Leu Arg Ala Cys Ala Asn Leu Gln Val
65                  70                  75                  80

Leu Met Leu Lys Ser Ser Arg Ile Asn Thr Ile Glu Gly Asp Ala Phe
                85                  90                  95

Tyr Ser Leu Gly Ser Leu Glu His Leu Asp Leu Ser Asp Asn His Leu
            100                 105                 110

Ser Ser Leu Ser Ser Ser Trp Phe Gly Pro Leu Ser Ser Leu Lys Tyr
        115                 120                 125

Leu Asn Leu Met Gly Asn Pro Tyr Gln Thr Leu Gly Val Thr Ser Leu
    130                 135                 140

Phe Pro Asn Leu Thr Asn Leu Gln Thr Leu Arg Ile Gly Asn Val Glu
145                 150                 155                 160

Thr Phe Ser Glu Ile Arg Arg Ile Asp Phe Ala Gly Leu Thr Ser Leu
                165                 170                 175

Asn Glu Leu Glu Ile Lys Ala Leu Ser Leu Arg Asn Tyr Gln Ser Gln
            180                 185                 190

Ser Leu Lys Ser Ile Arg Asp Ile His His Leu Thr Leu His Leu Ser
        195                 200                 205

Glu Ser Ala Phe Leu Leu Glu Ile Phe Ala Asp Ile Leu Ser Ser Val
```

```
              210                 215                 220
Arg Tyr Leu Glu Leu Arg Asp Thr Asn Leu Ala Arg Phe Gln Phe Ser
225                 230                 235                 240

Pro Leu Pro Val Asp Glu Val Ser Ser Pro Met Lys Lys Leu Ala Phe
                    245                 250                 255

Arg Gly Ser Val Leu Thr Asp Glu Ser Phe Asn Glu Leu Leu Lys Leu
                260                 265                 270

Leu Arg Tyr Ile Leu Glu Leu Ser Glu Val Glu Phe Asp Asp Cys Thr
            275                 280                 285

Leu Asn Gly Leu Gly Asp Phe Asn Pro Ser Glu Ser Asp Val Val Ser
        290                 295                 300

Glu Leu Gly Lys Val Glu Thr Val Thr Ile Arg Arg Leu His Ile Pro
305                 310                 315                 320

Gln Phe Tyr Leu Phe Tyr Asp Leu Ser Thr Val Tyr Ser Leu Leu Glu
                    325                 330                 335

Lys Val Lys Arg Ile Thr Val Glu Asn Ser Lys Val Phe Leu Val Pro
                340                 345                 350

Cys Ser Phe Ser Gln His Leu Lys Ser Leu Glu Phe Leu Asp Leu Ser
            355                 360                 365

Glu Asn Leu Met Val Glu Glu Tyr Leu Lys Asn Ser Ala Cys Lys Gly
        370                 375                 380

Ala Trp Pro Ser Leu Gln Thr Leu Val Leu Ser Gln Asn His Leu Arg
385                 390                 395                 400

Ser Met Gln Lys Thr Gly Glu Ile Leu Leu Thr Leu Lys Asn Leu Thr
                    405                 410                 415

Ser Leu Asp Ile Ser Arg Asn Thr Phe His Pro Met Pro Asp Ser Cys
                420                 425                 430

Gln Trp Pro Glu Lys Met Arg Phe Leu Asn Leu Ser Ser Thr Gly Ile
            435                 440                 445

Arg Val Val Lys Thr Cys Ile Pro Gln Thr Leu Glu Val Leu Asp Val
        450                 455                 460

Ser Asn Asn Asn Leu Asp Ser Phe Ser Leu Phe Leu Pro Arg Leu Gln
465                 470                 475                 480

Glu Leu Tyr Ile Ser Arg Asn Lys Leu Lys Thr Leu Pro Asp Ala Ser
                    485                 490                 495

Leu Phe Pro Val Leu Leu Val Met Lys Ile Arg Glu Asn Ala Val Ser
                500                 505                 510

Thr Phe Ser Lys Asp Gln Leu Gly Ser Phe Pro Lys Leu Glu Thr Leu
            515                 520                 525

Glu Ala Gly Asp Asn His Phe Val Cys Ser Cys Glu Leu Leu Ser Phe
        530                 535                 540

Thr Met Glu Thr Pro Ala Leu Ala Gln Ile Leu Val Asp Trp Pro Asp
545                 550                 555                 560

Ser Tyr Leu Cys Asp Ser Pro Pro Arg Leu His Gly His Arg Leu Gln
                    565                 570                 575

Asp Ala Arg Pro Ser Val Leu Glu Cys His Gln Ala Ala Leu Val Ser
                580                 585                 590

Gly Val Cys Cys Ala Leu Leu Leu Ile Leu Leu Val Gly Ala Leu
            595                 600                 605

Cys His His Phe His Gly Leu Trp Tyr Leu Arg Met Met Trp Ala Trp
        610                 615                 620

Leu Gln Ala Lys Arg Lys Pro Lys Lys Ala Pro Cys Arg Asp Val Cys
625                 630                 635                 640
```

```
Tyr Asp Ala Phe Val Ser Tyr Ser Glu Gln Asp Ser His Trp Val Glu
                645                 650                 655

Asn Leu Met Val Gln Gln Leu Glu Asn Ser Asp Pro Pro Phe Lys Leu
            660                 665                 670

Cys Leu His Lys Arg Asp Phe Val Pro Gly Lys Trp Ile Ile Asp Asn
        675                 680                 685

Ile Ile Asp Ser Ile Glu Lys Ser His Lys Thr Val Phe Val Leu Ser
    690                 695                 700

Glu Asn Phe Val Arg Ser Glu Trp Cys Lys Tyr Glu Leu Asp Phe Ser
705                 710                 715                 720

His Phe Arg Leu Phe Asp Glu Asn Asn Asp Ala Ala Ile Leu Val Leu
                725                 730                 735

Leu Glu Pro Ile Glu Arg Lys Ala Ile Pro Gln Arg Phe Cys Lys Leu
            740                 745                 750

Arg Lys Ile Met Asn Thr Lys Thr Tyr Leu Glu Trp Pro Leu Asp Glu
        755                 760                 765

Gly Gln Gln Glu Val Phe Trp Val Asn Leu Arg Thr Ala Ile Lys Ser
    770                 775                 780

<210> SEQ ID NO 3
<211> LENGTH: 8
<212> TYPE: PRT
<213> ORGANISM: Mus musculus

<400> SEQUENCE: 3

Gly Phe Thr Phe Thr Thr Tyr Gly
1               5

<210> SEQ ID NO 4
<211> LENGTH: 8
<212> TYPE: PRT
<213> ORGANISM: Mus musculus

<400> SEQUENCE: 4

Ile Tyr Pro Arg Asp Gly Ser Thr
1               5

<210> SEQ ID NO 5
<211> LENGTH: 11
<212> TYPE: PRT
<213> ORGANISM: Mus musculus

<400> SEQUENCE: 5

Ala Arg Leu Thr Gly Gly Thr Phe Leu Asp Tyr
1               5                   10

<210> SEQ ID NO 6
<211> LENGTH: 10
<212> TYPE: PRT
<213> ORGANISM: Mus musculus

<400> SEQUENCE: 6

Glu Ser Val Glu Tyr Tyr Gly Thr Ser Leu
1               5                   10

<210> SEQ ID NO 7
<211> LENGTH: 9
<212> TYPE: PRT
<213> ORGANISM: Mus musculus

<400> SEQUENCE: 7
```

```
Gln Gln Ser Arg Lys Leu Pro Trp Thr
1               5
```

<210> SEQ ID NO 8
<211> LENGTH: 167
<212> TYPE: PRT
<213> ORGANISM: Mus musculus

<400> SEQUENCE: 8

```
Met Ser Ser Pro Gln Ser Leu Lys Thr Leu Ile Leu Thr Met Gly Trp
1               5                   10                  15

Ser Trp Ile Phe Leu Phe Leu Leu Ser Gly Thr Ala Gly Val His Ser
            20                  25                  30

Gln Val Gln Leu Gln Gln Ser Gly Pro Glu Leu Val Asn Pro Gly Ala
        35                  40                  45

Ser Val Lys Leu Ser Cys Lys Ala Ser Gly Phe Thr Phe Thr Thr Tyr
    50                  55                  60

Gly Ile Asn Trp Val Lys Gln Gly Pro Gly Gln Gly Leu Glu Trp Ile
65                  70                  75                  80

Gly Trp Ile Tyr Pro Arg Asp Gly Ser Thr Asn Phe Asn Glu Asn Phe
                85                  90                  95

Lys Asp Lys Ala Ala Leu Thr Val Asp Thr Ser Ser Ser Thr Ala Tyr
            100                 105                 110

Met Glu Leu His Ser Leu Thr Ser Glu Asp Ser Ala Val Tyr Phe Cys
        115                 120                 125

Ala Arg Leu Thr Gly Gly Thr Phe Leu Asp Tyr Trp Gly Gln Gly Thr
    130                 135                 140

Thr Leu Thr Val Ser Ser Ala Lys Thr Thr Pro Pro Ser Val Tyr Pro
145                 150                 155                 160

Leu Ala Pro Gly Ser Ala Ala
                165
```

<210> SEQ ID NO 9
<211> LENGTH: 147
<212> TYPE: PRT
<213> ORGANISM: Mus musculus

<400> SEQUENCE: 9

```
Met Glu Ser Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Glu Tyr Tyr Gly Thr Ser Leu Met Gln Trp Tyr Gln Gln Lys Pro
    50                  55                  60

Gly Gln Pro Pro Lys Leu Leu Ile Phe Gly Ala Ser Asn Val Glu Ser
65                  70                  75                  80

Gly Val Pro Val Arg Phe Ser Gly Ser Gly Ser Gly Thr Asp Phe Ser
                85                  90                  95

Leu Asn Ile His Pro Val Glu Glu Asp Asp Ile Val Met Tyr Phe Cys
            100                 105                 110

Gln Gln Ser Arg Lys Leu Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140
```

-continued

Ser Ser Glu
145

<210> SEQ ID NO 10
<211> LENGTH: 111
<212> TYPE: PRT
<213> ORGANISM: Homo sapiens

<400> SEQUENCE: 10

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Phe Gly Ala Ser Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Met Tyr Phe Cys Gln Gln Ser Arg
                85                  90                  95

Lys Leu Pro Trp Thr Phe Gly Gly Gly Thr Lys Val Glu Ile Lys
            100                 105                 110

<210> SEQ ID NO 11
<211> LENGTH: 118
<212> TYPE: PRT
<213> ORGANISM: Homo sapiens

<400> SEQUENCE: 11

Gln Val Gln Leu Val Gln Ser Gly Ser Glu Leu Lys Lys Pro Gly Ala
1               5                   10                  15

Ser Val Lys Leu Ser Cys Lys Ala Ser Gly Phe Thr Phe Thr Thr Tyr
            20                  25                  30

Gly Ile Asn Trp Val Arg Gln Ala Pro Gly Gln Gly Leu Glu Trp Ile
        35                  40                  45

Gly Trp Ile Tyr Pro Arg Asp Gly Ser Thr Asn Phe Asn Glu Asn Phe
    50                  55                  60

Lys Asp Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Thr Gly Gly Thr Phe Leu Asp Tyr Trp Gly Gln Gly Thr
            100                 105                 110

Thr Val Thr Val Ser Ser
            115

<210> SEQ ID NO 12
<211> LENGTH: 218
<212> TYPE: PRT
<213> ORGANISM: Homo sapiens

<400> SEQUENCE: 12

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Tyr
            20                  25                  30

```
Gly Thr Ser Leu Met Gln Trp Tyr Gln Gln Lys Pro Gly Gln Pro Pro
            35                  40                  45

Lys Leu Leu Ile Phe Gly Ala Ser Asn Val Glu Ser Gly Val Pro Asp
 50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Met Tyr Phe Cys Gln Gln Ser Arg
                85                  90                  95

Lys Leu Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
    195                 200                 205

Val Thr Lys Ser Phe Asn Arg Gly Glu Cys
        210                 215

<210> SEQ ID NO 13
<211> LENGTH: 445
<212> TYPE: PRT
<213> ORGANISM: Homo sapiens

<400> SEQUENCE: 13

Gln Val Gln Leu Val Gln Ser Gly Ser Glu Leu Lys Lys Pro Gly Ala
1               5                   10                  15

Ser Val Lys Leu Ser Cys Lys Ala Ser Gly Phe Thr Phe Thr Thr Tyr
            20                  25                  30

Gly Ile Asn Trp Val Arg Gln Ala Pro Gly Gln Gly Leu Glu Trp Ile
        35                  40                  45

Gly Trp Ile Tyr Pro Arg Asp Gly Ser Thr Asn Phe Asn Glu Asn Phe
    50                  55                  60

Lys Asp Arg Ala Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Thr Gly Gly Thr Phe Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190
```

```
Ser Leu Gly Thr Lys Thr Tyr Thr Cys Asn Val Asp His Lys Pro Ser
            195                 200                 205
Asn Thr Lys Val Asp Lys Arg Val Glu Ser Lys Tyr Gly Pro Pro Cys
        210                 215                 220
Pro Pro Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 14
<211> LENGTH: 106
<212> TYPE: PRT
<213> ORGANISM: Macaca fascicularis

<400> SEQUENCE: 14

Asp Pro Gly Lys Val Glu Thr Val Thr Ile Arg Arg Leu His Ile Pro
1               5                   10                  15
Gln Phe Tyr Ser Phe Asn Asp Leu Ser Thr Leu Tyr Pro Leu Thr Glu
            20                  25                  30
Arg Val Lys Arg Ile Thr Val Glu Asn Ser Lys Val Phe Leu Val Pro
        35                  40                  45
Cys Leu Leu Ser Arg His Leu Lys Ser Leu Glu Tyr Leu Asp Leu Ser
    50                  55                  60
Glu Asn Leu Met Val Glu Glu Tyr Leu Lys Asn Ser Ala Cys Glu Asp
65                  70                  75                  80
Ala Trp Pro Ser Leu Gln Thr Leu Ile Leu Arg Gln Asn His Leu Ala
                85                  90                  95
Ser Leu Gly Lys Thr Gly Glu Thr Leu Leu
            100                 105
```

```
<210> SEQ ID NO 15
<211> LENGTH: 106
<212> TYPE: PRT
<213> ORGANISM: Sus scrofa

<400> SEQUENCE: 15

Ser Leu Gly Asn Val Glu Thr Leu Thr Val Arg Arg Leu His Ile Pro
1               5                   10                  15

Gln Phe Leu Phe Tyr Asp Leu Arg Ser Ile Tyr Ser Leu Thr Gly
            20                  25                  30

Ala Val Lys Arg Ile Thr Ile Glu Asn Ser Lys Val Phe Leu Val Pro
            35                  40                  45

Cys Ser Leu Ser Gln His Leu Lys Ser Leu Glu Tyr Leu Asp Leu Ser
    50                  55                  60

Glu Asn Leu Met Ser Glu Glu Tyr Leu Lys Asn Ser Ala Cys Glu His
65                  70                  75                  80

Ala Trp Pro Phe Leu His Thr Leu Ile Leu Arg Gln Asn His Leu Lys
                85                  90                  95

Ser Leu Glu Lys Thr Gly Glu Val Leu Val
            100                 105
```

METHODS AND COMPOSITIONS FOR THE TREATMENT OF PANCREATIC CANCER

FIELD OF THE INVENTION

The present invention relates to methods for the treatment or prevention of pancreatic cancer. Also provided are compositions for use in the treatment or prevention of pancreatic cancer.

BACKGROUND TO THE INVENTION

Toll-like Receptors (TLRs) form a family of pattern recognition receptors which have a key role in activating the innate immune response. Eleven TLRs have been identified in humans to date. The members of the TLR family are highly conserved, with most mammalian species having between ten to fifteen TLRs. Each TLR recognises specific pathogen-associated molecular signatures. Toll-like Receptor 2 (TLR2, CD282, TLR-2) is activated by peptidoglycan, lipoproteins and lipoteichoic acid. TLR2 is known to dimerise into two functional heterodimers. In particular, TLR2 is known to form a heterodimer with either Toll-like Receptor 1 (TLR1, TLR-1) or Toll-like Receptor 6 (TLR6, TLR-6). It is possible that further heterodimers are formed with Toll-like Receptor 4 (TLR4, TLR-4) and Toll-like Receptor 10 (TLR10, TLR-10). In addition to microbial derived components, TLRs are also known to recognize damage-associated molecular patterns (DAMPs). These are host endogenous molecules released and distributed following stress, tissue damage and cellular disease. WO 2005/028509 discloses a murine IgG1 anti-TLR2 antibody which was derived from hybridoma clone T2.5 (HyCult Biotechnology b.v., Cell Sciences, Canton, USA: catalogue number 1054—also known as OPN-301). WO2011/003925 describes a humanized version of T2.5 which is designated OPN-305.

Pancreatic cancer is the fourth most common cause of cancer related deaths in the United States and the eighth most common worldwide. It has one of the highest fatality rates of all cancers and is the fourth highest cancer killer among men and women. For all stages combined, the 1- and 5-year relative survival rates are 25% and 6% respectively. For local disease, the 5-year survival rate is approximately 20%. The median survival rates for locally advanced and for metastatic diseases, which collectively represent over 80% of individuals, are about 10 and 6 months respectively.

Treatment of pancreatic cancer depends on the stage of the cancer. Although only localized cancer is considered suitable for surgery with curative intent at present, only ~20% of cases present with localised disease at diagnosis. Surgery can also be performed for palliation if the malignancy is invading or compressing the duodenum or colon. In such cases, bypass surgery might overcome the obstruction and improve quality of life, but is not intended as a cure. In patients not suitable for resection with curative intent, palliative chemotherapy may be used to improve quality of life and gain a modest survival benefit. Gemcitabine was approved by the United States Food and Drug Administration in 1998 after a clinical trial reported improvements in quality of life and a 5-week improvement in median survival duration in patients with advanced pancreatic cancer. Gemcitabine has multiple immunostimulatory effects. It enhances antigen presentation by inducing tumour apoptosis and eliminates myeloid-derived suppressor cells. Cyclophosphamide enhances anti-tumour immunity by reducing the immunosuppressive effects of CD4+CD25+ regulatory T cells. Abraxane is licensed for use in breast cancer, but has shown some efficacy in pancreatic patients, albeit quite modest.

There is a need for improved methods for treating pancreatic cancer, in particular, metastatic pancreatic cancer. Metastasis is the leading cause of mortality in cancer patients. However, there are no effective therapies to target the development and progression of metastases in pancreatic cancer.

SUMMARY OF THE INVENTION

According to a first aspect of the present invention there is provided a method of treating or preventing pancreatic cancer comprising the step of:
  administering a therapeutically effective amount of a Toll-like receptor 2 (TLR2) antagonist to a subject in need thereof wherein the TLR2 antagonist is an antibody or an antigen binding fragment thereof.

Typically the treatment of the present invention inhibits or reduces tumour progression and/or increases apoptosis leading to enhanced survival of, and/or an improved quality of life for, the subject. The treatment may further enhance an immunostimulatory response and/or reduce immunosuppressive effects, for example, the immunosuppressive effects of regulatory T cells. Without wishing to be bound by theory, regulation of the immune response within the local tumour microenvironment may be dependent upon TLR2 activation. TLR2 is immunosuppressive so antagonising TLR2 may increase the Th1 immune response to fight pancreatic cancer. Infiltrating immune cells contribute to cancer growth and metastasis. Without wishing to be bound by theory, the effect observed may also involve targeting a target present on tumour cells.

Typically the TLR2 antibody or antigen binding fragment thereof has binding specificity to TLR2, typically human TLR2. Typically the TLR2 antibody or antigen binding fragment thereof has binding specificity to an epitope comprising amino acid residues of the extracellular domain of TLR2. The extracellular domain of the human form of TLR2 comprises 587 amino acid residues, specifically amino acids 1-587 of the 784 amino acid full length human TLR2 sequence shown as SEQ ID NO:1 and defined as Genbank Accession Number AAC 34133 (URL www.ncbi.nlm.nih.gov). Typically the antibody or antigen binding fragment thereof binds to the ligand binding region of TLR2. Typically the antibody or antigen binding fragment thereof inhibits or prevents dimerization of TLR2 with Toll-like Receptor 1 (TLR1) and/or Toll-like Receptor 6 (TLR6) by covering the interaction surface between TLR2 and TLR1 and/or TLR6. Typically the antibody or antigen binding fragment thereof suppresses the function of TLR2 irrespective of whether TLR2 forms a heterodimer with TLR1, Toll-like Receptor 4 (TLR4), TLR6 or Toll-like Receptor 10 (TLR10). Typically the binding region/interaction surface is located within leucine-rich repeat (LRR) regions 11 to 14 of TLR2. In certain embodiments the TLR2 antibody or antigen binding fragment thereof has binding specificity to an epitope comprising, consisting of or consisting essentially of LRR regions 11 to 14 of TLR2, or a sequence which has at least 85%, 90% or 95% sequence identity thereto.

In certain embodiments the TLR2 antibody or antigen binding fragment thereof binds to a non-continuous epitope comprising, consisting of or consisting essentially of amino acid residues His318 (H, histidine), Pro320 (P, proline), Arg321 (R, arginine) or Gln321 (Q, glutamine), Tyr323 (Y, tyrosine), Lys347 (K, lysine), Phe349 (F, phenylalanine), Leu371 (L, leucine), Glu375 (E, glutamic acid), Tyr376 (Y, tyrosine), and His398 (H, histidine) of SEQ ID NO: 1 or SEQ ID NO:2.

In certain embodiments the TLR2 antibody or antigen binding fragment thereof binds to a non-continuous epitope comprising, consisting of or consisting essentially of amino acid residues His318 (H, histidine), Pro320 (P, proline), Arg321 (R, arginine), Tyr323 (Y, tyrosine), Lys347 (K, lysine), Phe349 (F, phenylalanine), Leu371 (L, leucine), Glu375 (E, glutamic acid), Tyr376 (Y, tyrosine), and His398 (H, histidine) of SEQ ID NO: 1.

(human TLR2)
SEQ ID NO: 1
MPHTLWMVWV LGVIISLSKE ESSNQASLSC DRNGICKGSS

GSLNSIPSGL TEAVKSLDLS NNRITYISNS DLQRCVNLQA

LVLTSNGINT IEEDSFSSLG SLEHLDLSYN YLSNLSSSWF

KPLSSLTFLN LLGNPYKTLG ETSLFSHLTK LQILRVGNMD

TFTKIQRKDF AGLTFLEELE IDASDLQSYE PKSLKSIQNV

SHLILHMKQH ILLLEIFVDV TSSVECLELR DTDLDTFHFS

ELSTGETNSL IKKFTFRNVK ITDESLFQVM KLLNQISGLL

ELEFDDCTLN GVGNFRASDN DRVIDPGKVE TLTIRRLHIP

RFYLFYDLST LYSLTERVKR ITVENSKVFL VPCLLSQHLK

SLEYLDLSEN LMVEEYLKNS ACEDAWPSLQ TLILRQNHLA

SLEKTGETLL TLKNLTNIDI SKNSFHSMPE TCQWPEKMKY

LNLSSTRIHS VTGCIPKTLE ILDVSNNNLN LFSLNLPQLK

ELYISRNKLM TLPDASLLPM LLVLKISRNA ITTFSKEQLD

SFHTLKTLEA GGNNFICSCE FLSFTQEQQA LAKVLIDWPA

NYLCDSPSHV RGQQVQDVRL SVSECHRTAL VSGMCCALFL

LILLTGVLCH RFHGLWYMKM MWAWLQAKRK PRKAPSRNIC

YDAFVSYSER DAYWVENLMV QELENFNPPF KLCLHKRDFI

PGKWIIDNII DSIEKSHKTV FVLSENFVKS EWCKYELDFS

HFRLFEENND AAILILLEPI EKKAIPQRFC KLRKIMNTKT

YLEWPMDEAQ REGFWVNLRA AIKS

In certain embodiments the TLR2 antibody or antigen binding fragment thereof binds to a non-continuous epitope comprising, consisting of or consisting essentially of amino acid residues His318 (H, histidine), Pro320 (P, proline), Gln321 (Q, glutamine), Tyr323 (Y, tyrosine), Lys347 (K, lysine), Phe349 (F, phenylalanine), Leu371 (L, leucine), Glu375 (E, glutamic acid), Tyr376 (Y, tyrosine), and His398 (H, histidine) of murine TLR2 (SEQ ID NO: 2). SEQ ID NO:2 shows the amino acid murine TLR2 sequence defined as Genbank Accession Number NP_036035 (Mus musculus).

(murine TLR2)
SEQ ID NO: 2
MLRALWLFWI LVAITVLFSK RCSAQESLSC DASGVCDGRS

RSFTSIPSGL TAAMKSLDLS FNKITYIGHG DLRACANLQV

LMLKSSRINT IEGDAFYSLG SLEHLDLSDN HLSSLSSSWF

GPLSSLKYLN LMGNPYQTLG VTSLFPNLTN LQTLRIGNVE

TFSEIRRIDF AGLTSLNELE IKALSLRNYQ SQSLKSIRDI

HHLTLHLSES AFLLEIFADI LSSVRYLELR DTNLARFQFS

PLPVDEVSSP MKKLAFRGSV LTDESFNELL KLLRYILELS

EVEFDDCTLN GLGDFNPSES DVVSELGKVE TVTIRRLHIP

QFYLFYDLST VYSLLEKVKR ITVENSKVFL VPCSFSQHLK

SLEFLDLSEN LMVEEYLKNS ACKGAWPSLQ TLVLSQNHLR

SMQKTGEILL TLKNLTSLDI SRNTFHPMPD SCQWPEKMRF

LNLSSTGIRV VKTCIPQTLE VLDVSNNNLD SFSLFLPRLQ

ELYISRNKLK TLPDASLFPV LLVMKIRENA VSTFSKDQLG

SFPKLETLEA GDNHFVCSCE LLSFTMETPA LAQILVDWPD

SYLCDSPPRL HGHRLQDARP SVLECHQAAL VSGVCCALLL

LILLVGALCH HFHGLWYLRM MWAWLQAKRK PKKAPCRDVC

YDAFVSYSEQ DSHWVENLMV QQLENSDPPF KLCLHKRDFV

PGKWIIDNII DSIEKSHKTV FVLSENFVRS EWCKYELDFS

HFRLFDENND AAILVLLEPI ERKAIPQRFC KLRKIMNTKT

YLEWPLDEGQ QEVFWVNLRT AIKS

The above identified epitope in humans or mice is a functional epitope for receptor dimerization or inhibition thereof. Typically the epitope is bound by the TLR2 antagonistic antibodies T2.5 and OPN-305. Binding of the identified epitope by an antagonistic antibody or an antigen binding fragment thereof results in antagonism of TLR2 biological function, in particular activation and signalling. In particular, binding by the antibody or antigen binding fragment thereof serves to inhibit activation of the TLR2 receptor, irrespective of whether a TLR2 heterodimer is formed with another TLR, such as TLR1, TLR6, TLR4 or TLR10. Furthermore, antibodies binding to this epitope have been shown to cross-react with TLR2 from human, pig and monkey, indicating this to be a critical epitope in a highly conserved region of TLR2.

In certain embodiments the antibody is selected from the group consisting of a human antibody, a humanised antibody, a chimeric antibody, a monoclonal antibody, a polyclonal antibody, a synthetic antibody, a camelid antibody, a shark antibody and an in-vitro antibody. In certain embodiments an antigen binding fragment may be used. The antigen binding fragment may be derived from any of the aforementioned antibodies. In certain embodiments the antigen binding fragment is selected from the group consisting of a Fab fragment, a scFv fragment, a Fv fragment and a dAb fragment. In certain embodiments the antibody comprises two complete heavy chains and two complete light chains, or an antigen binding fragment thereof. In certain embodiments the antibody is of the isotype IgG, IgA, IgE or IgM, or an antigen binding fragment thereof. In certain embodiments where the antibody is of the isotype IgG, the antibody may be of the subtype IgG1, IgG2 or IgG3, or an antigen binding fragment thereof. In certain embodiments the antibody is of the subtype IgG4, or an antigen binding fragment thereof. The antibody or antigen binding fragment may bind to an inhibitory epitope present on TLR2 with a dissociation constant (Kd) of from about $10^{-7}$M to about $10^{-11}$M. More particularly the antibody or antigen binding fragment thereof may bind to mammalian (e.g. human or murine) TLR2 with a $K_D$ of $4 \times 10^{-8}$ M or less. Even more particularly the antibody or antigen binding fragment thereof may bind to human TLR2 with a $K_D$ of $3 \times 10^{-8}$ M or less. In certain embodiments the antibody is an isolated antibody or an antigen binding fragment thereof.

In certain embodiments the antibody or antigen binding fragment comprises a heavy chain variable region comprising the heavy chain variable region complementarity regions of the murine IgG1 anti-TLR2 antibody derived from hybridoma clone T2.5 (HyCult Biotechnology b.v., Cell Sciences, Canton, USA: catalogue number 1054) and/or a light chain variable region comprising the light chain variable region complementarity regions of the murine IgG1 anti-TLR2 antibody derived from hybridoma clone T2.5 (HyCult Biotechnology b.v., Cell Sciences, Canton, USA: catalogue number 1054). In certain embodiments the antibody or antigen binding fragment comprises a heavy chain variable region comprising a complementarity determining region 1 (CDR1) region comprising the amino acid sequence Gly-Phe-Thr-Phe-Thr-Thr-Tyr-Gly (SEQ ID NO:3), a CDR2 region comprising the amino acid sequence Ile-Tyr-Pro-Arg-Asp-Gly-Ser-Thr (SEQ ID NO:4) and a CDR3 region comprising the amino acid sequence Ala-Arg-Leu-Thr-Gly-Gly-Thr-Gly-Phe-Leu-Asp-Tyr (SEQ ID NO:5), and/or a light chain variable region comprising a CDR1 region comprising the amino acid sequence Glu-Ser-Val-Glu-Tyr-Tyr-Gly-Thr-Ser-Leu (SEQ ID NO:6), a CDR2 region comprising the amino acid sequence Gly-Ala-Ser and a CDR3 region comprising the amino acid sequence Gln-Gln-Ser-Arg-Lys-Leu-Pro-Trp-Thr (SEQ ID NO:7).

In certain embodiments the antibody or antigen binding fragment comprises a heavy chain variable region of the murine IgG1 anti-TLR2 antibody derived from hybridoma clone T2.5 (HyCult Biotechnology b.v., Cell Sciences, Canton, USA: catalogue number 1054) and/or a light chain variable region of the murine IgG1 anti-TLR2 antibody derived from hybridoma clone T2.5 (HyCult Biotechnology b.v., Cell Sciences, Canton, USA: catalogue number 1054). In certain embodiments the heavy chain variable region comprises or consists of the amino acid sequence as depicted in SEQ ID NO:8, or a sequence which has at least 85%, 90%, 95%, 96%, 97%, 98% or 99% amino acid sequence identity over a length of at least 20, and up to all, amino acids of the amino acid sequence of SEQ ID NO:8, and/or the light chain variable region comprises or consists of the amino acid sequence as depicted in SEQ ID NO:9, or a sequence which has at least 85%, 90%, 95%, 96%, 97%, 98% or 99% amino acid sequence identity over a length of at least 20, and up to all, amino acids of the amino acid sequence of SEQ ID NO:9.

In certain embodiments the antibody or antigen binding fragment comprises a heavy chain variable region of a humanised version of the murine IgG1 anti-TLR2 antibody derived from hybridoma clone T2.5 (HyCult Biotechnology b.v., Cell Sciences, Canton, USA: catalogue number 1054) and/or a light chain variable region of a humanised version the murine IgG1 anti-TLR2 antibody derived from hybridoma clone T2.5 (HyCult Biotechnology b.v., Cell Sciences, Canton, USA: catalogue number 1054). In certain embodiments the antibody or antigen binding fragment comprises a heavy chain variable region of the OPN-305 antibody as described in WO2011/003925 and/or a light chain variable region of the OPN-305 antibody as described in WO2011/003925. In certain embodiments the antibody or antigen binding fragment comprises a light chain variable domain comprising or consisting of an amino acid sequence of SEQ ID NO:10, or a sequence which has at least 85%, 90%, 95%, 96%, 97%, 98% or 99% amino acid sequence identity over a length of at least 20, and up to all, amino acids of the amino acid sequence of SEQ ID NO:10, and/or a heavy chain variable domain comprising or consisting of an amino acid sequence of SEQ ID NO:11, or a sequence which has at least 85%, 90%, 95%, 96%, 97%, 98% or 99% amino acid sequence identity over a length of at least 20, and up to all, amino acids of the amino acid sequence of SEQ ID NO:11. Typically, the antibody or antigen binding fragment specifically binds to TLR2 and does not bind to CD32. Typically the antibody or antigen binding fragment thereof mediates TLR2 antagonism independently of binding of the antibody or antigen binding fragment thereof to TLR2.

In certain embodiments the antibody or antigen binding fragment comprises a heavy chain of a humanised version of the murine IgG1 anti-TLR2 antibody derived from hybridoma clone T2.5 (HyCult Biotechnology b.v., Cell Sciences, Canton, USA: catalogue number 1054) and/or a light chain of a humanised version the murine IgG1 anti-TLR2 antibody derived from hybridoma clone T2.5 (HyCult Biotechnology b.v., Cell Sciences, Canton, USA: catalogue number 1054), or an antigen binding fragment thereof. In certain embodiments the antibody or antigen binding fragment comprises a heavy chain of the OPN-305 antibody as described in WO2011/003925 and/or a light chain of the OPN-305 antibody as described in WO2011/003925. In certain embodiments the light chain comprises or consists of the amino acid sequence of SEQ ID NO:12, or a sequence which has at least 85%, 90%, 95%, 96%, 97%, 98% or 99% amino acid sequence identity over a length of at least 20, and up to all, amino acids of the amino acid sequence of SEQ ID NO:12, and/or the heavy chain comprises the amino acid sequence of SEQ ID NO:13, or a sequence which has at least 85%, 90%, 95%, 96%, 97%, 98% or 99% amino acid sequence identity over a length of at least 20, and up to all, amino acids of the amino acid sequence of SEQ ID NO:13. Typically, the antibody or antigen binding fragment is a fully humanised antibody. In certain embodiments the variable domain of the heavy chain is joined to a constant domain derived from an antibody of the subclass immunoglobulin G, isotype 4. In certain embodiments amino acid residue 241 of a hinge region of the heavy chain is substituted from a serine residue to a proline residue. In certain embodiments the antibody or antigen binding fragment binds to mammalian Toll-like Receptor 2 with a $K_D$ of $1 \times 10^{-8}$ M or less. In certain embodiments the antibody or antigen binding fragment binds to mammalian (e.g. human or murine) TLR2 with a $K_D$ of $4 \times 10^{-8}$ M or less. In certain embodiments the antibody or antigen binding fragment binds to human TLR2 with a $K_D$ of $3 \times 10^{-8}$ M or less.

In certain embodiments the antibody or antigen binding fragment is derived from hybridoma clone T2.5 (HyCult Biotechnology b.v., Cell Sciences, Canton, USA: catalogue number 1054), or is a humanised version thereof. In certain embodiments the antibody is a murine IgG1 anti-TLR2 antibody derived from hybridoma clone T2.5 (HyCult Biotechnology b.v., Cell Sciences, Canton, USA: catalogue number 1054), or a humanised version or antigen binding fragment thereof. In certain embodiments the humanised version thereof is the OPN-305 antibody, as described in WO2011/003925.

In certain embodiments, the antibody or antigen binding fragment thereof is part of a chimeric antigen receptor (CAR) T-cell. Typically, the CAR comprises the antibody or antigen binding fragment thereof. Typically the antibody or antigen binding fragment may be any antibody or antigen binding fragment as described above, e.g. OPN-305 or an antigen binding fragment thereof, such as a Fab fragment. Chimeric antigen receptors (CARs), also known as artificial T-cell receptors, are genetically engineered receptors which graft a new specificity onto an immune effector cell. Typically, these receptors are used to graft the specificity of a monoclonal antibody onto a T-cell and this may be carried out using a lentiviral vector. CAR T-cells may be used as a therapy for cancer, using a technique called adoptive cell transfer in which T-cells are removed from a subject and modified so that they express receptors specific to the particular form of cancer. The T-cells are reintroduced into the subject with the ability to recognize and kill targeted cancer cells and trigger T-cell killing mechanisms.

In certain embodiments, the antibody or antigen binding fragment thereof forms part of a bifunctional or multifunctional ligand. Typically the antibody or antigen binding fragment may be any antibody or antigen binding fragment as described above, e.g. OPN-305 or an antigen binding fragment thereof, such as a Fab fragment.

Also described herein are TLR2 antagonists comprising a nucleic acid encoding an antibody or antigen binding fragment as described above, or a vector comprising said nucleic acid.

Also described herein are TLR2 antagonists comprising an inhibitory nucleic acid which inhibits the expression of at least one nucleic acid which encodes TLR2 protein. The TLR2 antagonist may be selected from the group consisting of anti-sense oligonucleotides, triple helix molecules, anti-sense DNA, anti-sense RNA, ribozyme, iRNA, miRNA, siRNA and shRNA. Accordingly, a therapeutically effective amount of an inhibitory nucleic acid, such as an RNAi (RNA interference) agent, for example an interfering ribonucleic acid (such as siRNA or shRNA) or a transcription template thereof, such as a DNA encoding an shRNA may be administered to a subject in order to block the expression of the TLR2 protein. The inhibitory nucleic acid may be an anti-sense RNA molecule. Antisense causes suppression of gene expression and involves single stranded RNA fragments which physically bind to mRNA, thus blocking mRNA translation. Techniques for the preparation of inhibitory nucleic acids are known to persons skilled in the art.

Suppression of the function of TLR2 can be achieved by means of reducing the amount of ligand which is available to bind to and activate membrane bound TLR2. A reduction in the amount of ligand which is available to bind membrane bound TLR2 results in a downregulation of TLR2-mediated signalling. Accordingly, the TLR2 antagonist may be a soluble form of recombinant TLR2 (sTLR2), or a functional fragment thereof. The soluble form of TLR2 competes with the membrane bound form of TLR2 for TLR2 specific binding ligands. This competitive binding results in the soluble form of TLR2 effectively "mopping up" available TLR2 ligand with an associated reduction in the binding and activation of membrane bound TLR2.

The soluble form of TLR2 may be prepared by a recombinant technique. A soluble form of TLR2 typically comprises the extracellular domain of TLR2 only, and hence the intracellular and transmembrane domains of TLR2 as defined in Genbank Accession Number AAC 34133 (SEQ ID NO:1) are absent. The soluble form of TLR2 may comprise amino acids 1 to 587 of SEQ ID NO:1. The soluble TLR2 sequence may be modified by means of the addition, deletion or substitution of one or more amino acid residues. Accordingly, the soluble form of TLR2 may be derived from a truncated form of the full length membrane bound TLR2 amino acid sequence or, in addition to a deletion and/or substitution of the amino acids residues relating to the intracellular and/or transmembrane domains in the membrane bound form of TLR2, a deletion and/or substitution may further be made to the amino acid residues of the extracellular domain. Any such truncation or deletion and/or substitution of the amino acid residues of the extracellular domain of the TLR2 may be made so long as the modified form of TLR2 is soluble and capable of binding a ligand which can bind to at least one epitope present on the membrane bound form of TLR2.

In certain embodiments the TLR2 antibody or antigen binding fragment thereof is targeted to the pancreas or TLR2 expressed on pancreatic cells or tissue. In certain embodiments the TLR2 antibody or antigen binding fragment thereof is targeted specifically to tumour cells. Targeting may be by any suitable means known to the person skilled in the art, such as localised delivery, the use of a delivery vector or a targeting means, such as an antibody which has binding specificity for a cell surface target expressed on pancreatic cells and/or tumour tissue. The targeting of the TLR2 antibody or antigen binding fragment thereof in this way is advantageous as systemic administration of the TLR2 antibody or antigen binding fragment thereof may result in global immunosuppression of the TLR2 receptor and accordingly TLR2 mediated signalling which may be undesirable in some instances. Targeting of the TLR2 antibody or antigen binding fragment thereof may be provided through the formation of a fusion protein, wherein said fusion protein is comprised of a TLR2 antibody or antigen binding fragment thereof conjoined to a secondary peptide, typically the Fc receptor binding protein derived from the heavy chain of an immunoglobulin, typically a human immunoglobulin. The Fc domain has been extensively used to prolong the circulatory half-life of therapeutic proteins.

In certain embodiments the TLR2 antibody or antigen binding fragment thereof binds to the epitope present on the extracellular domain of TLR2 with an affinity constant (Ka) of at least $10^{-6}$M.

In certain embodiments the method comprises the step of administering a second TLR2 antagonist to the subject. For example, a TLR2 antagonistic antibody may be administered to prevent the activation of TLR2 and an inhibitory nucleic acid may also be administered to inhibit the expression of TLR2.

In certain embodiments the method of the invention further comprises a step of administering a therapeutically effective amount of a secondary therapeutic compound suitable for use in the treatment or prevention of pancreatic cancer. Combination therapies comprising a TLR2 antagonist as described above and a secondary therapeutic compound may show significant benefits over mono-therapeutics alone. Said secondary therapeutic compound may be a chemotherapeutic agent.

In certain embodiments, the secondary therapeutic compound or chemotherapeutic agent increases TLR2 expression. In certain embodiments, the secondary therapeutic compound or chemotherapeutic agent increases the overall percentage of myeloid infiltrate. The increased infiltration of myeloid cells is known to correlate with increased TLR2 expression as F4/80 and CD11b positive cells (markers for monocytes and neutrophils in particular) are known to co-express TLR2. For example, Arslan et al. 2010 (Circulation 2010; 121; 80-90) shows a correlation between TLR2 and CD11b (FIGS. 3C and D and the results section), Harokopakis & Hajishengallis 2005 (Eur. J. Immunol. 2005. 35: 1201-1210) shows that CD11b and TLR2 expression on the same cells are crucial for the innate immune response to

*P. gingivalis* bacteria, Angel et al. (International Immunology, Vol. 19, No. 11, pp. 1271-1279) shows that CD14+ cells co-express CD11b, Bryan et al. (Arthritis & Rheumatism, Vol. 52, No. 9, September 2005, pp. 2936-2946) shows that greater than 95% of F4/80+ cells co-express TLR2 and Zhou et al. 2008 (Journal of Neuroimmunology 194 (2008) 70-82) shows that CD11b+ microglial cells (brain macrophages) respond to TLR ligands including the TLR2/1 ligand Pam 3, but that CD11b negative cells do not which further adds weight to the co-expression of TLR2 with CD11b.

In certain embodiments, the secondary therapeutic compound or chemotherapeutic agent enhances the anti-tumour microenvironment, typically at a later time point.

The chemotherapeutic agent may be selected from one or more of the group consisting of gemcitabine, cyclophosphamide, abraxane, fluorouracil (5-FU), oxaliplatin, FolFox, Folfiri and Folfirinox. In certain embodiments the secondary therapeutic compound or chemotherapeutic agent is gemcitabine. In certain embodiments the secondary therapeutic compound or chemotherapeutic agent is or comprises fluorouracil (5-FU). In certain embodiments the secondary therapeutic compound or chemotherapeutic agent is or comprises oxaliplatin. In certain embodiments the secondary therapeutic compound or chemotherapeutic agent is Folfirinox. In certain embodiments the secondary therapeutic compound or chemotherapeutic agent is cyclophosphamide. The tumour stroma consists of diverse cellular populations including macrophages, fibroblasts and lymphocytes. Without wishing to be bound by theory, it is hypothesised that TLR2 inhibition may affect the tumour stroma and as such allow better penetration of a co-administered chemotherapeutic agent.

In certain embodiments the secondary therapeutic compound is gemcitabine. The inventor has surprisingly recognised that treatment with an antagonistic TLR2 antibody or antigen binding fragment thereof and gemcitabine has an especially increased synergistic effect in treating pancreatic cancer as compared with treatment with either the TLR2 antibody or antigen binding fragment thereof or gemcitabine alone. In particular, treatment with a TLR2 antibody or antigen binding fragment thereof plus gemcitabine may synergistically increase survival/life span and suppress metastasis (e.g. liver metastasis) as compared with treatment with either agent alone. The treatment may further enhance an immunostimulatory response and/or reduce immunosuppressive effects, for example, the immunosuppressive effects of regulatory T cells. Furthermore, treatment with a TLR2 antibody or antigen binding fragment thereof plus gemcitabine may synergistically reduce tumour proliferation and enhance apoptosis. Without wishing to be bound by theory, the inventor of the present invention considers that the combination of a TLR2 antibody or antigen binding fragment thereof with gemcitabine might prove to be beneficial due to the known effect of gemcitabine in depleting myeloid derived suppressor cells, therefore contributing to an overall net outcome of immune activation when combined with a TLR2 antagonist.

In certain embodiments the secondary therapeutic compound is administered simultaneously, sequentially or separately to the TLR2 antibody or antigen binding fragment thereof. In certain embodiments the secondary therapeutic compound is administered simultaneously to the TLR2 antibody or antigen binding fragment thereof.

In certain embodiments the method of the invention further comprises a step of administering a therapeutically effective amount of a tertiary therapeutic compound suitable for use in the treatment or prevention of pancreatic cancer. Said tertiary therapeutic compound may be a chemotherapeutic agent, typically selected from one or more of the group consisting of gemcitabine, cyclophosphamide, abraxane, fluorouracil (5FU), oxaliplatin, FolFox, Folfiri and Folfirinox, more typically cyclophosphamide or abraxane. Cyclophosphamide has a well described ablational effect on regulatory T cells. In certain embodiments, the tertiary therapeutic compound is abraxane. In certain embodiments the secondary therapeutic compound is gemcitabine and the tertiary therapeutic compound is selected from the group consisting of cyclophosphamide, abraxane, fluorouracil (5FU), oxaliplatin, FolFox, Folfiri and Folfirinox, typically cyclophosphamide or abraxane. In certain embodiments the secondary therapeutic compound is gemcitabine and the tertiary therapeutic compound is abraxane. The addition of abraxane to an antagonistic TLR2 antibody and gemcitabine surprisingly increased overall survival in a mouse model of pancreatic cancer. Without wishing to be bound by theory, the inventor of the present invention considers that the combination of a TLR2 antibody or antigen binding fragment thereof with cyclophosphamide and optionally a secondary therapeutic compound such as gemcitabine might prove to be beneficial in contributing to an overall net outcome of immune activation.

In certain embodiments the tertiary therapeutic compound is administered simultaneously, sequentially or separately to the TLR2 antibody or antigen binding fragment thereof and/or the secondary therapeutic compound.

In certain embodiments, the TLR2 antibody or antigen binding fragment thereof is administered to the subject prior to, during or following the subject undergoing a surgical procedure, such as resection.

Typically the subject is suffering from pancreatic cancer. The subject may have one or more tumours. In certain embodiments the pancreatic cancer is metastatic. In alternative embodiments the pancreatic cancer is locally advanced. Alternatively, the pancreatic cancer may be localised. In certain embodiments the subject may be at risk of developing pancreatic cancer. Subjects at risk of developing pancreatic cancer may be identified, for example, using genetic testing, in particular, by testing individuals having a family history of pancreatic cancer. In certain embodiments, tumour cells from the subject are pre-screened, for example, at the earlier staging/endoscopy stage, for TLR2 expression. Typically treatment is administered to subjects with tumour cells showing TLR2 expression. This ensures the subject's tumour will respond to TLR2 antagonism. Typically treatment is administered to subjects with later stage tumours.

Typically, the subject is a mammal, most typically a human.

Typically the TLR2 antibody or antigen binding fragment thereof is an antagonist of human TLR2, for example the human TLR2 sequence shown in SEQ ID NO:1, or an amino acid sequence having at least 90% sequence identity thereto. In certain embodiments the TLR2 antibody or antigen binding fragment thereof is an antagonist of murine TLR2, for example the murine TLR2 sequence shown in SEQ ID NO:2, or an amino acid sequence having at least 90% sequence identity thereto.

According to a further aspect of the invention there is provided a composition comprising a TLR2 antibody or antigen binding fragment thereof for use in the treatment or prophylaxis of pancreatic cancer in a subject.

The embodiments described for the first aspect of the invention also apply for this aspect of the invention where applicable. In particular, the TLR2 antibody or antigen binding fragment thereof may be a TLR2 antibody or antigen binding fragment thereof as described above. The secondary and/or tertiary therapeutic compound may be selected as described above.

In certain embodiments the composition is provided for simultaneous, separate or sequential administration with a secondary therapeutic compound. In certain embodiments the composition comprises a secondary therapeutic compound, e.g. a chemotherapeutic agent. In certain embodiments, the secondary therapeutic compound or chemotherapeutic agent increases TLR2 expression. In certain embodiments, the secondary therapeutic compound or chemotherapeutic agent increases the overall percentage of myeloid infiltrate. Said secondary therapeutic compound or chemotherapeutic agent may be selected from one or more of the group consisting of gemcitabine, cyclophosphamide, abraxane, fluorouracil (5FU), oxaliplatin, FolFox, Folfiri and Folfirinox, typically gemcitabine or cyclophosphamide. In certain embodiments, the chemotherapeutic agent is gemcitabine. In certain embodiments, the chemotherapeutic agent is or comprises oxaliplatin or fluorouracil. In certain embodiments, the chemotherapeutic agent is Folfirinox.

In certain embodiments the composition is provided for simultaneous, separate or sequential administration with a tertiary therapeutic compound. In certain embodiments the composition comprises a tertiary therapeutic compound. Said tertiary therapeutic compound may be a chemotherapeutic agent, typically selected from one or more of the group consisting of gemcitabine, cyclophosphamide, abraxane, fluorouracil (5FU), oxaliplatin, FolFox, Folfiri and Folfirinox, even more typically cyclophosphamide or abraxane. In certain embodiments, the tertiary therapeutic compound is abraxane.

According to a further aspect of the invention there is provided use of a composition comprising a TLR2 antibody or antigen binding fragment thereof in the preparation of a medicament for the treatment or prophylaxis of pancreatic cancer in a subject.

The embodiments described for the first aspect of the invention also apply for this aspect of the invention where applicable. In particular, the TLR2 antibody or antigen binding fragment thereof may be a TLR2 antibody or antigen binding fragment thereof as described above. The secondary and/or tertiary therapeutic compound may be selected as described above.

In certain embodiments, the medicament is a combined medicament comprising a secondary therapeutic compound. In certain embodiments the composition comprises a secondary therapeutic compound. In certain embodiments the composition is provided for simultaneous, separate or sequential administration with a secondary therapeutic agent. In certain embodiments, the secondary therapeutic compound is a chemotherapeutic agent. In certain embodiments, the secondary therapeutic compound or chemotherapeutic agent increases TLR2 expression. In certain embodiments, the secondary therapeutic compound or chemotherapeutic agent increases the overall percentage of myeloid infiltrate. The secondary therapeutic compound or chemotherapeutic agent may be selected from one or more of the group consisting of gemcitabine, cyclophosphamide, abraxane, fluorouracil (5FU), FolFox, Folfiri and Folfirinox. In certain embodiments the secondary therapeutic compound is gemcitabine. In certain embodiments, the chemotherapeutic agent is or comprises oxaliplatin or fluorouracil. In certain embodiments, the chemotherapeutic agent is Folfirinox.

In certain embodiments, the medicament further comprises a tertiary therapeutic compound. In certain embodiments the composition comprises a tertiary therapeutic compound. In certain embodiments the composition is provided for simultaneous, separate or sequential administration with a tertiary therapeutic agent. Said tertiary therapeutic compound may be a chemotherapeutic agent, typically selected from one or more of the group consisting of gemcitabine, cyclophosphamide, abraxane, fluorouracil (5FU), FolFox, Folfiri and Folfirinox, more typically cyclophosphamide or abraxane. In certain embodiments, the tertiary therapeutic compound is abraxane.

The TLR2 antibody or antigen binding fragment thereof may be provided in the form of a pharmaceutical composition comprising a TLR2 antibody or antigen binding fragment thereof as described above and at least one pharmaceutically acceptable carrier, diluent, solubilizer, emulsifier, preservative and/or adjuvant. In certain embodiments, the composition includes a secondary therapeutic compound as described above, typically a chemotherapeutic agent selected from the group consisting of gemcitabine, cyclophosphamide, abraxane, fluorouracil (5FU), oxaliplatin, FolFox, Folfiri and Folfirinox, more typically gemcitabine. In certain embodiments, the secondary therapeutic compound or chemotherapeutic agent increases TLR2 expression when administered alone, that is, when administered without a TLR2 antagonistic agent. In certain embodiments, the secondary therapeutic compound or chemotherapeutic agent increases the overall percentage of myeloid infiltrate when administered alone, that is, when administered without a TLR2 antagonistic agent. In certain embodiments, the composition includes a tertiary therapeutic compound as described above, typically a chemotherapeutic agent selected from the group consisting of gemcitabine, cyclophosphamide, abraxane, fluorouracil (5FU), oxaliplatin, FolFox, Folfiri and Folfirinox, more typically abraxane.

Also provided is a CAR T-cell comprising a gene modified autologous T-cell which is engineered to express an antibody against TLR2 or an antigen binding fragment thereof. Typically the antibody or antigen binding fragment may be an antibody or antigen binding fragment as described above, e.g. OPN-305 or an antigen binding fragment thereof, such as a Fab fragment.

Further provided is a bifunctional or a multifunctional ligand comprising an antibody against TLR2 or an antigen binding fragment thereof. Typically the antibody or antigen binding fragment may be an antibody or antigen binding fragment as described above, e.g. OPN-305 or an antigen binding fragment thereof, such as a Fab fragment.

In a further aspect, the present invention extends to a screening method for the identification of compounds for use in treatment or prevention of pancreatic cancer, the method comprising the steps of:
  (a) providing candidate compounds, e.g. antibodies having binding specificity for TLR2 or antigen binding fragments thereof;
  (b) contacting the candidate compounds with TLR2; and
  (c) identifying compounds which antagonise TLR2;
wherein antagonism of TLR2 is indicative of utility of the compound in the treatment or prevention of pancreatic cancer.

In a further aspect, the present invention extends to a screening method for the identification of compounds for use in treatment or prevention of pancreatic cancer, the method comprising the steps of:
  (a) providing candidate compounds which are antagonists of TLR2 function, e.g. antibodies having binding specificity for TLR2 or antigen binding fragments thereof;
  (b) contacting the candidate compounds with TLR2; and (c) identifying compounds which bind to TLR2 within the region of amino acid residues His318 (H, histidine), Pro320 (P, proline), Arg321 (R, arginine) or Gln321 (Q, glutamine), Tyr323 (Y, tyrosine), Lys347 (K, lysine), Phe349 (F, phenylalanine), Leu371 (L, leucine), Glu375 (E, glutamic acid), Tyr376 (Y, tyrosine), and His398 (H, histidine) of SEQ ID NO: 1 or SEQ ID NO:2;

wherein binding in this region is indicative of utility of the compound in the treatment or prevention of pancreatic cancer.

BRIEF DESCRIPTION OF THE FIGURES

The present invention will now be described with reference to the following examples which are provided for the purpose of illustration and are not intended to be construed as being limiting on the present invention wherein:

FIG. 4(b) shows survival proportions of same and FIG. 4(c) shows a comparison of survival curves.

FIG. 5(b) shows survival proportions of same and FIG. 5(c) shows a comparison of survival curves.

FIG. 6(b) shows survival proportions of same and FIG. 6(c) shows a comparison of survival curves.

FIG. 11 shows an alignment of the dimerization site (human (SEQ ID NO: 11, mouse (SEQ ID NO: 2), monkey (SEQ ID NO: 14), and pig (SEQ ID NO: 15)) and mutation analysis.

DETAILED DESCRIPTION OF THE INVENTION

Figure 1:
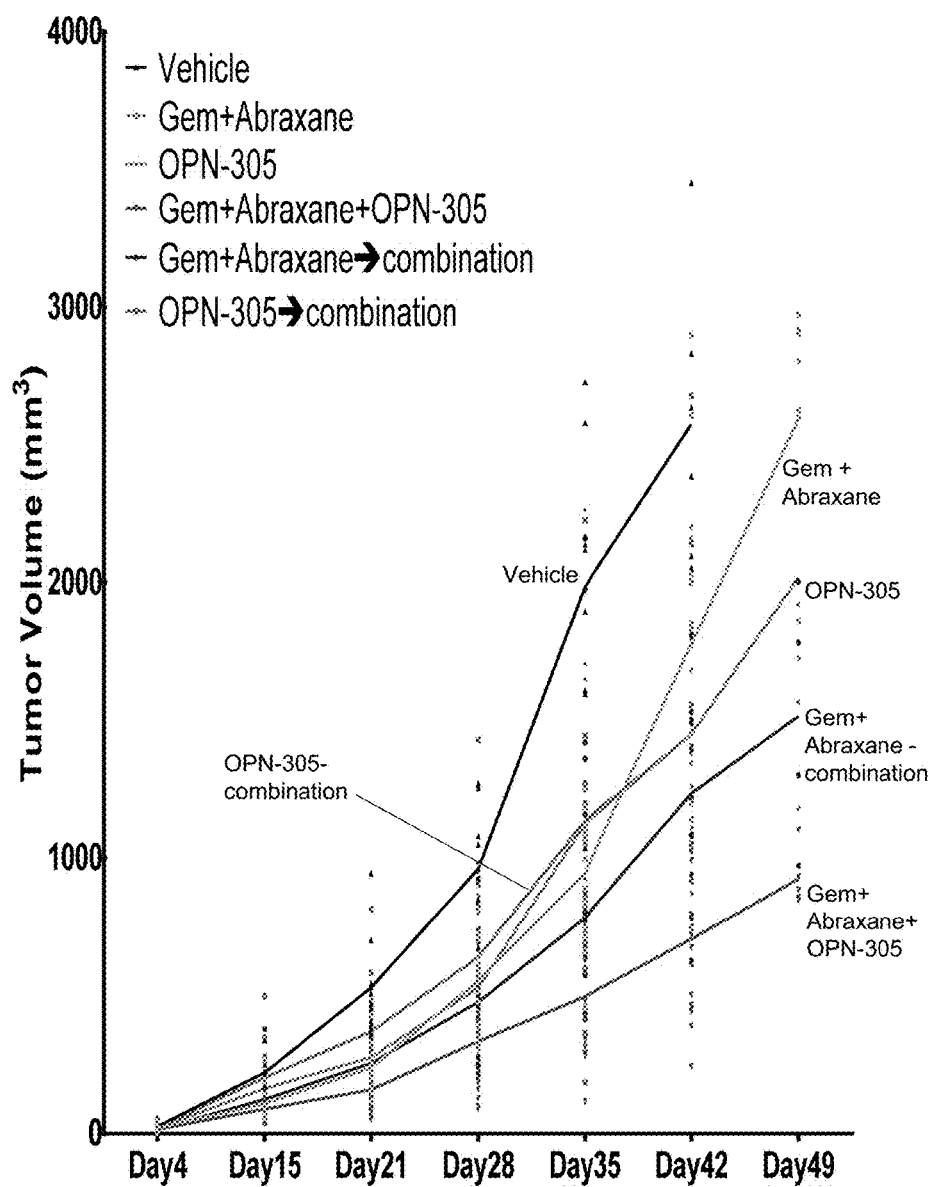
FIG. 1 shows tumour volume for mice in different treatment groups over a period of 49 days.

A TLR2 neutralising antibody may be used to treat pancreatic cancer. In particular, percentage survival of mice is increased following treatment. Tumour progression is reduced. Without wishing to be bound by theory, the inventor predicts that treatment with a TLR2 neutralising antibody enhances an anti-tumour microenvironment. The effect observed may also involve targeting a target present on tumour cells as TLR2 is also expressed by malignant cells. Furthermore, TLR2 inhibition augments the efficacy of chemotherapeutic agents in a mouse model of pancreatic cancer. When the TLR2 neutralising antibody is combined with a secondary therapeutic compound, such as gemcitabine, a surprising synergistic effect may be observed as compared with treatment with either agent alone. In particular, a combination of gemcitabine and TLR2 neutralising antibody may synergistically reduce liver metastasis and tumour progression and increase survival. This may be further enhanced when abraxane is added.

Definitions

As herein defined, "Toll-like Receptor 2" may be also referred to as TLR2, TLR-2 or CD282. Typically, the TLR2 is human TLR2. Alternatively, the TLR2 is murine TLR2. In further embodiments, the TLR2 is a homologue or orthologue of human TLR2 which is derived from any mammal other than a human or mouse, for example, a cow or rat. In certain embodiments the TLR2 antibody is cross-reactive in that it mediates the suppression of TLR2 function in TLR2 derived from different species.

As herein defined, an agent is a "TLR2 antagonist" if the agent suppresses or blocks the activation or function of TLR2. The agent may inhibit or block binding of a ligand or binding compound to TLR2. This inhibition of TLR2 ligand binding may be achieved by a number of means, for example, through binding to the extracellular domain of TLR2 and partially or fully blocking the TLR2 ligand binding site, or by binding at a site other than the known TLR2 ligand binding site and inducing a conformational change upon binding which results in the TLR2 ligand binding site being altered in a manner which prevents TLR2 ligand binding or TLR2 activation. Further, the agent may inhibit or suppress intracellular signalling mediated by TLR2 following ligand binding and/or TLR2 activation. Intracellular signalling mediated following TLR2 activation and signalling results in the activation of transcription factors and the expression of genes which mediate a pro-inflammatory immune response. The agent may suppress or block TLR2 protein or gene expression, for example, by inhibiting the expression of a gene encoding a TLR2 protein.

As herein defined, the terms "blocks" and "blocking" when used in relation to TLR2 gene expression mean silencing the expression of at least one gene which results in the expression of the TLR2 protein. Gene silencing is the switching off of the expression of a gene by a mechanism other than genetic modification. Gene silencing can be mediated at the transcriptional level or at the post-transcriptional level. Transcriptional gene silencing can result in a gene being inaccessible to transcriptional machinery, and can be mediated, for example, by means of histone modifications. Post-transcriptional gene silencing results from the mRNA of a gene being destroyed, thus preventing an active gene product, such as a protein, in the present case the TLR2 protein.

The term "specifically binds" or "binding specificity" refers to the ability of a TLR2 binding compound (e.g. antibody or antigen binding fragment thereof) to bind to a target epitope present on TLR2 with a greater affinity than it binds to a non-target epitope. In certain embodiments specific binding refers to binding to a particular target epitope which is present on TLR2 with an affinity which is at least 10, 50, 100, 250, 500, or 1000 times greater than the affinity for a non-target epitope. Binding affinity may be determined by an affinity ELISA assay, a BIAcore assay, a kinetic method or by an equilibrium/solution method.

As herein defined, an "epitope" refers to a plurality of amino acid residues which are capable of being recognised by, and bound to by, a binding compound, such as a ligand, small molecule or antibody. Epitopes are generally comprised of chemically active surface groups and have specific three-dimensional structural characteristics, as well as specific charge characteristics which contribute to the three-dimensional structure of the epitope. The TLR2 antagonist antagonises the functional activity of TLR2 and as such binds to an epitope known as an inhibiting epitope or an inhibitory epitope. An "inhibiting" or "inhibitory" epitope means an epitope present on TLR2 that when bound by a binding compound, such as a small molecule or an antibody, results in the loss of biological activity of TLR2, for example due to the binding compound preventing the binding of TLR2 by a TLR2 agonist. The epitope that is present on TLR2, and which is bound by the binding compounds in order to antagonise TLR2 function, may comprise five or more amino acid residues.

The TLR2 antagonist of the invention binds to a non-contiguous epitope. A "non-contiguous epitope" is an epitope that is comprised of a series of amino acid residues that are non-linear in alignment, such that the residues are spaced or grouped in a non-continuous manner along the length of a polypeptide sequence. The non-contiguous epitope described herein is a discontinuous scattered epitope wherein the residues which contribute to the epitope are provided in three or more groups of linear amino acid sequences arranged along the length of the TLR2 polypeptide.

As used herein, the term "subject" refers to an animal, preferably a mammal and in particular a human.

The term "consisting essentially of" as used herein means that the invention necessarily includes the listed items and is open to including unlisted items that do not materially affect the basic and novel properties of the invention.

The nomenclature used to describe the polypeptide constituents of the present invention follows the conventional practice wherein the amino group (N) is presented to the left and the carboxyl group to the right of each amino acid residue.

The expression "amino acid" as used herein is intended to include both natural and synthetic amino acids, and both D and L amino acids. A synthetic amino acid also encompasses chemically modified amino acids, including, but not limited to, salts, and amino acid derivatives such as amides. Amino acids can be modified by methylation, amidation, acetylation or substitution with other chemical groups which can change the circulating half life without adversely affecting their biological activity.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived Furthermore the term "fusion protein" as used herein can also be taken to mean a fusion polypeptide, fusion peptide or the like, or may also be referred to as an immunoconjugate. The term "fusion protein" refers to a molecule in which two or more subunit molecules, typically polypeptides, are covalently or non-covalently linked.

As used herein, the term "therapeutically effective amount" means an amount which is sufficient to show benefit to the subject to whom the composition or TLR2 antagonist is administered, e.g. by reducing the severity of at least one symptom of pancreatic cancer, by reducing tumour size, by suppressing tumour growth, by inhibiting angiogenesis, by suppressing metastasis, by suppressing a T regulatory cell response and/or by promoting a Th1 response.

As used herein, the term "treatment" and associated terms such as "treat" and "treating" means the reduction of the progression or severity of pancreatic cancer or at least one symptom thereof, e.g. by reducing tumour size, by suppressing tumour growth, by inhibiting angiogenesis, by suppressing metastasis, by suppressing a T regulatory cell response and/or by promoting a Th1 response. The term "treatment" refers to any regimen that can benefit a subject. The treatment may be in respect of an existing pancreatic cancer condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that the subject is treated until total recovery. Similarly, "prophylactic" does not necessarily mean that the subject will not eventually contract a disease condition.

Unless otherwise defined, all technical and scientific terms used herein have the meaning commonly understood by a person who is skilled in the art in the field of the present invention.

Throughout the specification, unless the context demands otherwise, the terms "comprise" or "include", or variations such as "comprises" or "comprising", "includes" "including" will be understood to imply the inclusion of a stated integer or group of integers, but not the exclusion of any other integer or group of integers.

As used herein, terms such as "a", an and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

Antibodies

The TLR2 antagonist is an antibody or an antigen binding fragment thereof. An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb or Fd, and a bi-specific antibody.

In certain embodiments the antibody may be a camelid antibody, in particular a camelid heavy chain antibody. Further, the antibody fragment may be a domain antibody or a nanobody derived from a camelid heavy chain antibody. In certain embodiments the antibody may be a shark antibody or a shark derived antibody.

In certain embodiments the antibody is an "isolated antibody", this meaning that the antibody is (1) free of at least some proteins with which it would normally be found, (2) is essentially free of other proteins from the same source, e.g., from the same species, (3) is expressed by a cell from a different species, or (4) does not occur in nature.

As antibodies can be modified in a number of ways, the term "antibody" should be construed as covering any binding member or substance having a binding domain with the required specificity. The antibody of the invention may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included.

The constant region of the antibody may be of any suitable immunoglobulin subtype. In certain embodiments the subtype of the antibody may be of the class IgA, IgM, IgD and IgE where a human immunoglobulin molecule is used. Such an antibody may further belong to any subclass, e.g. IgG1, IgG2a, IgG2b, IgG3 and IgG4.

Fragments of a whole antibody can perform the function of antigen binding. Examples of such binding fragments are a Fab fragment comprising or consisting of the VL, VH, CL and CH1 antibody domains; an Fv fragment consisting of the VL and VH domains of a single antibody; a F(ab')2 fragment; a bivalent fragment comprising two linked Fab fragments; a single chain Fv molecule (scFv), wherein a VH domain and a VL domain are linked by a peptide linker which allows the two domains to associate to form an antigen binding site; and a bi-specific antibody, which may be multivalent or multispecific fragments constructed by gene fusion.

A fragment of an antibody for use in the present invention generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

A "derivative" of such an antibody or of a fragment of a TLR2 specific antibody means an antibody or polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having TLR2 binding activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

In certain embodiments humanized antibodies are also provided. A humanised antibody may be a modified antibody having the hypervariable region of a TLR2 specific antibody and the constant region of a human antibody. Thus the binding member may comprise a human constant region. The variable region other than the hypervariable region may also be derived from the variable region of a human antibody and/or may also be derived from a TLR2 specific antibody. In other cases, the entire variable region may be derived from a murine monoclonal TLR2 specific antibody and the antibody is said to be chimerised.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin.

A hybridoma or other cell producing an antibody may be subject to genetic mutation or other changes, which may or may not alter the binding specificity of antibodies produced.

In certain embodiments the therapeutically effective amount comprises the antibody in a range chosen from 1 μg/kg to 20 mg/kg, 1 g/kg to 10 mg/kg 1 μg/kg to 1 mg/kg 10 μg/kg to 1 mg/kg 10 μg/kg to 100 pg/kg and 500 pg/kg to 1 mg/kg.

Production of Antibodies

The antibodies provided for use in the present invention may be provided by a number of techniques. For example, a combinatorial screening technique such as a phage display-based biopanning assay may be used to in order to identify amino acid sequences which have binding specificity to TLR2, in particular the binding epitopes described above. Such phage display biopanning techniques involve the use of phage display libraries, which are utilised in methods which identify suitable epitope binding ligands in a procedure which mimics immune selection, through the display of antibody binding fragments on the surface of filamentous bacteria. Phage with specific binding activity are selected. The selected phage can thereafter be used in the production of chimeric, CDR-grafted, humanised or human antibodies. Antibodies can be tested for their ability to antagonise TLR2 function using methods known in the art.

In further embodiments the antibody is a monoclonal antibody, which may be produced using any suitable method which produces antibody molecules by continuous cell lines in culture. Chimeric antibodies or CDR-grafted antibodies are further provided for use in the present invention. In certain embodiments, the antibodies for use in the invention may be produced by the expression of recombinant DNA in a host cell.

In certain embodiments the monoclonal antibodies may be human antibodies, produced using transgenic animals, for example, transgenic mice, which have been genetically modified to delete or suppress the expression of endogenous murine immunoglobulin genes, with loci encoding for human heavy and light chains being expressed in preference, this resulting in the production of fully human antibodies.

In certain embodiments the TLR2 antagonist is a binding fragment which is derived from an antibody, for example, an antibody binding fragment, such as a Fab, F(ab')2, Fv or a single chain Fv (scFV).

In certain embodiments the TLR2 antibody comprises a polyclonal antibody, a chimeric antibody, a synthesized or synthetic antibody, a fusion protein or fragment thereof, a natural or synthetic chemical compound or a peptidomimetic.

The antibodies or antigen fragments for use in the present invention may also be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acid encoding them by use of nucleic acid in an expression system.

Nucleic acid for use in accordance with the present invention may comprise DNA or RNA and may be wholly or partially synthetic. In a preferred aspect, nucleic acid for use in the invention codes for antibodies or antibody fragments of the invention as defined above. The skilled person will be able to determine substitutions, deletions and/or additions to such nucleic acids which will still provide an antibody or antibody fragment of the present invention.

Nucleic acid sequences encoding antibodies or antibody fragments for use with the present invention can be readily prepared by the skilled person. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NS0 mouse myeloma cells. A common, preferred bacterial host is *E. coli*. The expression of antibodies and antibody fragments in prokaryotic cells such as *E. coli* is well established in the art. Expression in eukaryotic cells in culture is also available to those skilled in the art as an option for production of a binding member. General techniques for the production of antibodies are well known to the person skilled in the field.

In certain embodiments of the invention, recombinant nucleic acids comprising an insert coding for a heavy chain variable domain and/or for a light chain variable domain of antibodies are provided. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

Recombinant DNA technology may be used to improve the antibodies for use in the invention. Thus, chimeric antibodies may be constructed in order to decrease the immunogenicity thereof in diagnostic or therapeutic applications. Moreover, immunogenicity within, for example, a transgenic organism such as a pig, may be minimised, by altering the antibodies by CDR grafting in a technique analogous to humanising antibodies. In order to reduce immunogenicity within a human recipient, the invention may employ recombinant nucleic acids comprising an insert coding for a heavy chain variable domain of an antibody fused to a human constant domain. Likewise the invention concerns recombinant DNAs comprising an insert coding for a light chain variable domain of an antibody fused to a human constant domain kappa or lambda region.

Antibodies may moreover be generated by mutagenesis of antibody genes to produce 5 artificial repertoires of antibodies. This technique allows the preparation of antibody libraries. Antibody libraries are also available commercially. Hence, the present invention advantageously employs artificial repertoires of immunoglobulins, preferably artificial scFv repertoires, as an immunoglobulin source in order to identify binding molecules which have specificity for the epitope described above.

Antibody Selection Systems

Immunoglobulins which are able to bind to and antagonise TLR2 and which accordingly may be used in the methods of the invention can be identified using any technique known to the skilled person. Such immunoglobulins may be conveniently isolated from libraries comprising artificial repertoires of immunoglobulin polypeptides. A "repertoire" refers to a set of molecules generated by random, semi-random or directed variation of one or more template molecules, at the nucleic acid level, in order to provide a multiplicity of binding specificities. Methods for generating repertoires are well characterised in the art.

Any library selection system may be used in conjunction with the invention. Selection protocols for isolating desired members of large libraries are known in the art, as typified by phage display techniques. Such systems, in which diverse peptide sequences are displayed on the surface of filamentous bacteriophage, have proven useful for creating libraries of antibody fragments (and the nucleotide sequences that encode them) for the in-vitro selection and amplification of specific antibody fragments that bind a target antigen. The nucleotide sequences encoding the VH and VL regions are linked to gene fragments which encode leader signals that direct them to the periplasmic space of *E. coli* and as a result the resultant antibody fragments are displayed on the surface of the bacteriophage, typically as fusions to bacteriophage coat proteins (for example pIII or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straight forward.

Methods for the construction of bacteriophage antibody display libraries and lambda phage expression libraries are well known in the art.

An alternative to the use of phage or other cloned libraries is to use nucleic acid, preferably RNA, derived from the B cells of an animal which has been immunised with the selected target, e.g. the TLR2 epitope described above.

Isolation of V-region and C-region mRNA permits antibody fragments, such as Fab or Fv, to be expressed intracellularly. Briefly, RNA is isolated from the B cells of an immunised animal, for example from the spleen of an immunised mouse or the circulating B cells of a llama, and PCR primers used to amplify VH and VL cDNA selectively from the RNA pool. The VH and VL sequences thus obtained are joined to make scFv antibodies. PCR primer sequences may be based on published VH and VL sequences.

A method for producing polypeptides comprises culturing host cells transformed with a recombinant expression vector encoding a polypeptide under conditions that promote expression of the polypeptide, then recovering the expressed polypeptides from the culture. The person skilled in the art will recognise that the procedure for purifying the expressed polypeptides will vary according to such factors as the type of host cells employed, and whether the polypeptide is intracellular, membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, avian, microbial, viral, bacterial, or insect gene. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired (*E. coli*) host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide during translation, but allows secretion of polypeptide from the cell.

Suitable host cells for expression of polypeptides include higher eukaryotic cells and yeast. Prokaryotic systems are also suitable. Mammalian cells, and in particular CHO cells are particularly preferred for use as host cells.

Administration

The TLR2 antagonist may be administered alone, but will preferably be administered as a pharmaceutical composition, which will generally comprise a suitable pharmaceutically acceptable excipient, diluent or carrier selected depending on the intended route of administration. Examples of suitable pharmaceutical carriers include water, glycerol, ethanol and other GRAS reagents.

The TLR2 antagonist may be administered to a subject in need of treatment via any suitable route. As detailed herein, it is preferred that the composition is administered parenterally by injection or infusion. Examples of preferred routes for parenteral administration include, but are not limited to, intravenous, intracardial, intraarterial, intraperitoneal, intramuscular, intracavity, subcutaneous, transmucosal, inhalation and transdermal. Routes of administration may further include topical and enteral, for example, mucosal (including pulmonary), oral, nasal, rectal.

The composition may be delivered as an injectable composition. For intravenous, intramuscular, intradermal or subcutaneous application, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

The actual dose administered, and rate and time-course of administration, will depend on, and can be determined with due reference to, the nature and severity of the condition which is being treated, as well as factors such as the age, sex and weight of the subject to be treated and the route of administration. Further due consideration should be given to the properties of the composition, for example, its binding activity and in-vivo plasma life, the concentration of the antagonist in the formulation, as well as the route, site and rate of delivery.

Dosage regimens can include a single administration of the composition of the invention, or multiple administrative doses of the composition. The compositions can further be administered sequentially or separately with other therapeutics and medicaments which are used for the treatment of pancreatic cancer.

The composition may be administered as a single dose or as repeated doses. Examples of dosage regimens which can be administered to a subject can be selected from the group comprising, but not limited to, 1 µg/kg/day through to 20 mg/kg/day, 1 µg/kg/day through to 10 mg/kg/day, 10 µg/kg/day through to 1 mg/kg/day.

The TLR2 antagonist may be orally administered to the subject, for example, at a dose of from about 1 mg/kg to about 10 mg/kg of the subject's body weight per day. In certain embodiments the dose of the TLR2 antagonist is from about 100 mg per day to about 1000 mg per day. In certain further embodiments the dose of the TLR2 antagonist is from about 200 mg per day to about 300 mg per day. In certain embodiments the TLR2 antagonist is administered to the subject parenterally with a dosage range of between about 0.001 mg/kg to 1.0 mg/kg of the subject's body weight. Typically, the TLR2 antagonist is administered to the subject for a time and under conditions sufficient to down regulate the level and/or activity of TLR2.

Candidate Compounds

The present invention provides an assay method for identifying compounds for use in the treatment or prevention of pancreatic cancer. The method comprises identifying compounds which bind to and antagonise TLR2, for example, identifying compounds which bind the same epitope on TLR2 as that bound by the T2.5 and OPN-305 antibodies.

Typically the candidate compound is an antibody or an antigen binding fragment thereof.

The precise format of the candidate compound screening assay may be varied by those skilled in the art using routine skill and knowledge. Combinatorial library technology provides an efficient way of testing a potentially vast number of different substances for the ability to bind to an epitope. The amount of candidate compound which may be added to an assay will normally be determined by trial and error depending upon the type of compound used. Typically, from about 0.01 to 100 nM concentrations of the candidate compound may be used, for example from 0.1 to 10 nM. Greater concentrations may be used when the candidate binding compound is a peptide. A candidate compound which has affinity and binding specificity for TLR2, e.g. the binding epitope described herein, may be isolated and/or purified and tested for its ability to antagonise TLR2 function. The compound may thereafter be manufactured and/or used to modulate TLR2 functional activity in the treatment or prevention of pancreatic cancer.

Sequence Identity

The present invention extends to the use of sequences having at least 80%, 85%, 90%, 95%, 97%, 98% or 99% amino acid sequence identity to the sequences of the TLR2 antagonists described herein. Such sequences or polypeptides may comprise a sequence which is substantially homologous to a polypeptide having the amino acid sequence of a TLR2 antagonist described herein, but may have a different amino acid sequence because of one or more deletions, insertions, or substitutions. The substantially homologous polypeptide may include 1, 2 or more amino acid alterations. Alternatively, or in addition, the substantially homologous polypeptide may consist of a truncated version of a TLR2 antagonist described herein which has been truncated by 1, 2 or more amino acids. In certain embodiments sequence identity is over a length of at least 20, 25, 30, 35 or 40 amino acids of the amino acid sequence in question. In certain embodiments sequence identity is over the complete length of the amino acid sequence in question (e.g. any one of SEQ ID NO:8, 9, 10, 11, 12 and/or 13).

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the nucleic acids for use herein may be variants that differ from a native DNA sequence because of one or more deletions, insertions or substitutions, but that encode a biologically active polypeptide.

As used herein, percentage amino acid sequence identity may be determined, using any method known to the person skilled in the art, for example, by comparing sequence information using the GAP computer program, version 6.0 described by Devereux et al. (Nucl. Acids Res. 12:387, 1984) and available from the University of Wisconsin Genetics Computer Group (UWGCG).

The present invention will now be described with reference to the following examples which are provided for the purpose of illustration and are not intended to be construed as being limiting on the present invention.

EXAMPLE 1—Therapeutic Efficacy of TLR2 Targeting in Pancreatic Cancer in Preclinical Setting—Orthotopic Implantation of KPC Cell Line from SubQ Tumours Materials and Methods A preclinical mouse model of pancreatic cancer was established where a KPC cell line derived from the genetically engineered 'KPC' mouse with pancreas-specific mutant Kras and mutant TP53 genetic background (LSL-KrasG12D; p53R172H, Pdx1-Cre) backcrossed several generations with C57Bl/6 mice was implanted as allograft, orthotopically in the pancreas of C57bl/6 (B6) mice. In brief, a subcutaneous tumour was first established by injecting 2.5 million cells under the skin of C57Bl/6 mice. Ten days later, the tumour was excised and chopped into smaller pieces, roughly 1 mm$^3$ in size, and implanted orthotopically into pancreas of C57Bl/6 mice. For orthotopic implantation into the pancreas, each mouse was anesthetized with 2.5% Avertin, 0.013 ml/g B.W. All surgical procedures were performed under aseptic conditions with use of sterile gloves and autoclaved instruments. The skin was disinfected with betadine followed by alcohol and this procedure was repeated twice. A left lateral oblique incision was made through the skin and then through the body wall just below the stomach. The pancreas was exteriorized with forceps, tumor implant placed inside the pancreas and the pancreas restored to its native condition. The body wall was sutured with resorbable suture followed by closure of the skin with metal clips. An analgesic (Buprenophine 0.05 mg/kg SQ BID) was given directly after and every 12 hours for 48 hours following surgery. Body temperature was maintained during post-operative care and whenever necessary, subcutaneous injection of normal saline (0.2-0.5 ml) was administered to maintain hydration post-operatively. The growth of orthotopic tumours were measured over the period of 12-16 weeks by non-invasive ultrasound (Vevo2100, VisualSonic). Tumour volume data was plotted using GraphPad Prism software. Mice were euthanized when the maximum permissible tumour size limit of 2 cm$^3$ was reached or other criteria of pain and distress were met. Mice were inoculated with a tumour of 5-10 mm$^3$, randomised into treatment groups as below when the tumour was approximately 25 mm$^3$ and treatment was commenced when the tumours were approximately 100 mm$^3$. The orthotopically implanted tumours were measured by ultrasound 5 days post-surgery and randomized into various treatment arms as below:

1. Vehicle (PBS)
2. Gemcitabine (Gem)+Abraxane (Abrax)
3. OPN-305 (antibody)
4. Gemcitabine+Abraxane+OPN-305 ("concurrent combination therapy")
5. Gemcitabine+Abraxane (2 weeks) followed by concurrent combination therapy
6. OPN-305 (2 weeks) followed by concurrent combination therapy Dosing Scheme:
Gemcitabine (100 mg/kg; i.p., twice weekly beginning day 0)
Abraxane (10 mg/kg; i.v., day 0 only)
OPN-305 (10 mg/kg; i.v., once weekly)

Results

Figure 2A:
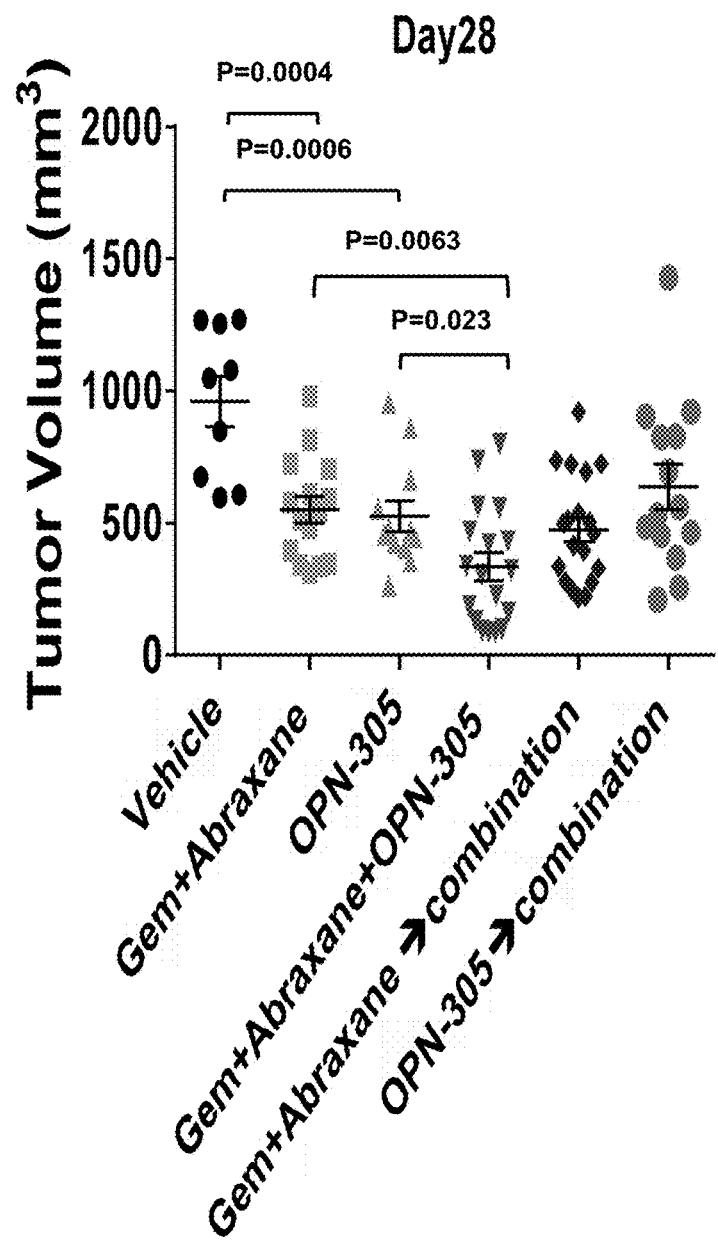
FIGS. 2a-2c show tumour volume for mice in different treatment groups on day 28 (FIG. 2(a)), day 35 (FIG. 2(b)) and day 42 (FIG. 2(c)).
Figure 2B:
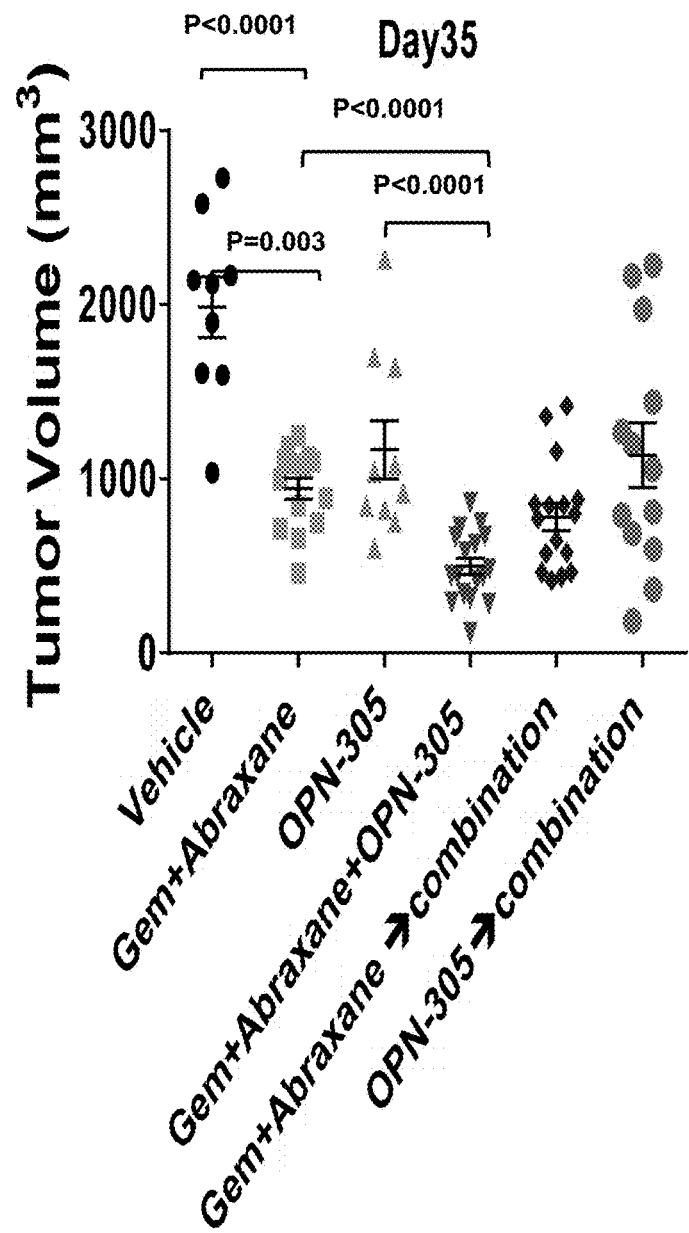
Figure 2C:
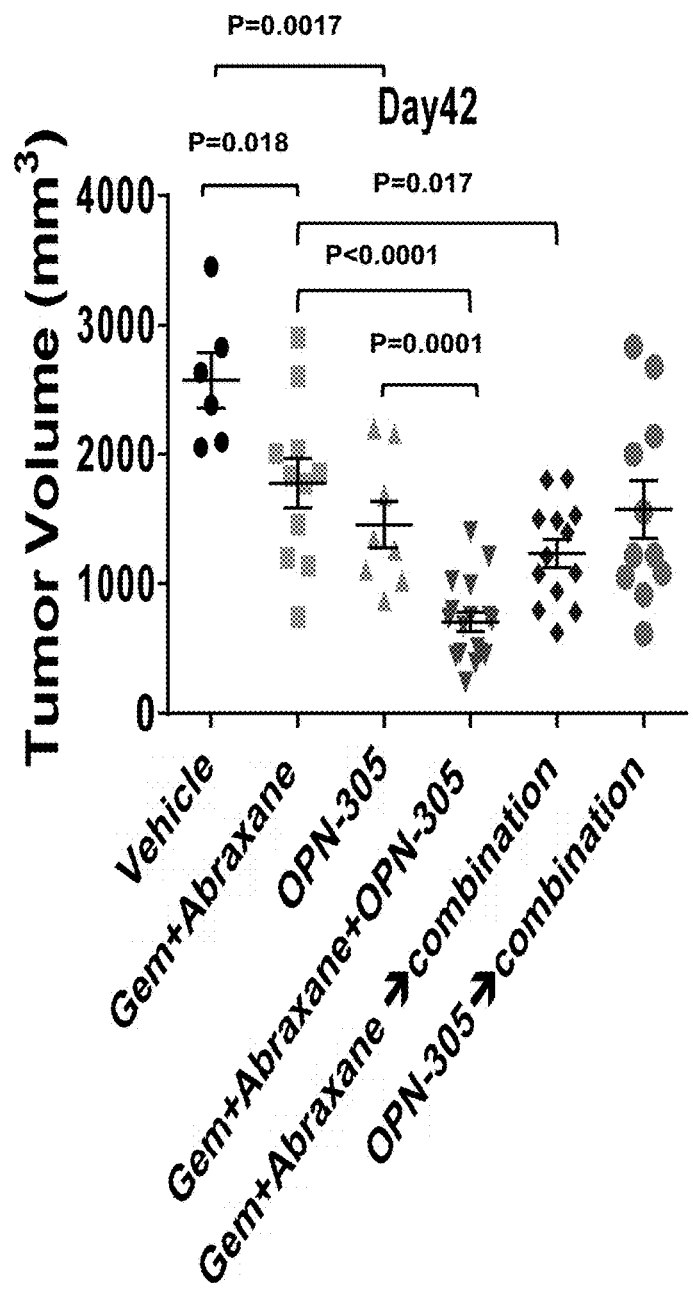
Figure 3A:
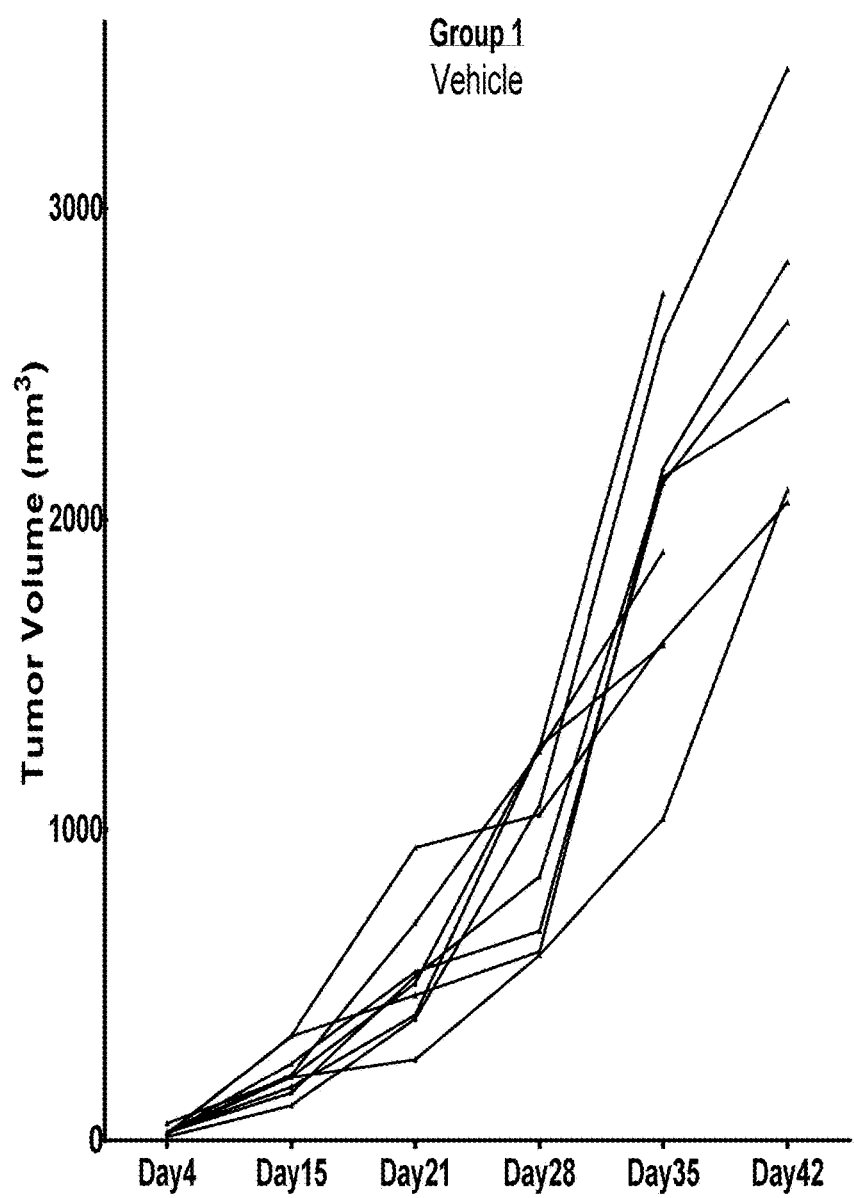
FIGS. 3a-3f are graphs showing tumour volume over a period of 42/49 days for mice treated with vehicle (Group 1—FIG. 3(a)), Gemcitabine (Gem) and Abraxane (Group 2—FIG. 3(b)), OPN-305 (Group 3—FIG. 3(c)), Gem and Abraxane and OPN-305 (Group 4—FIG. 3(d)), Gem and Abraxane followed by a concurrent combination of OPN-305, Gem and Abraxane (Group 5—FIG. 3(e)) and OPN305 following by a concurrent combination of OPN-305, Gem and Abraxane (Group 6—FIG. 3(f)).
Figure 3B:
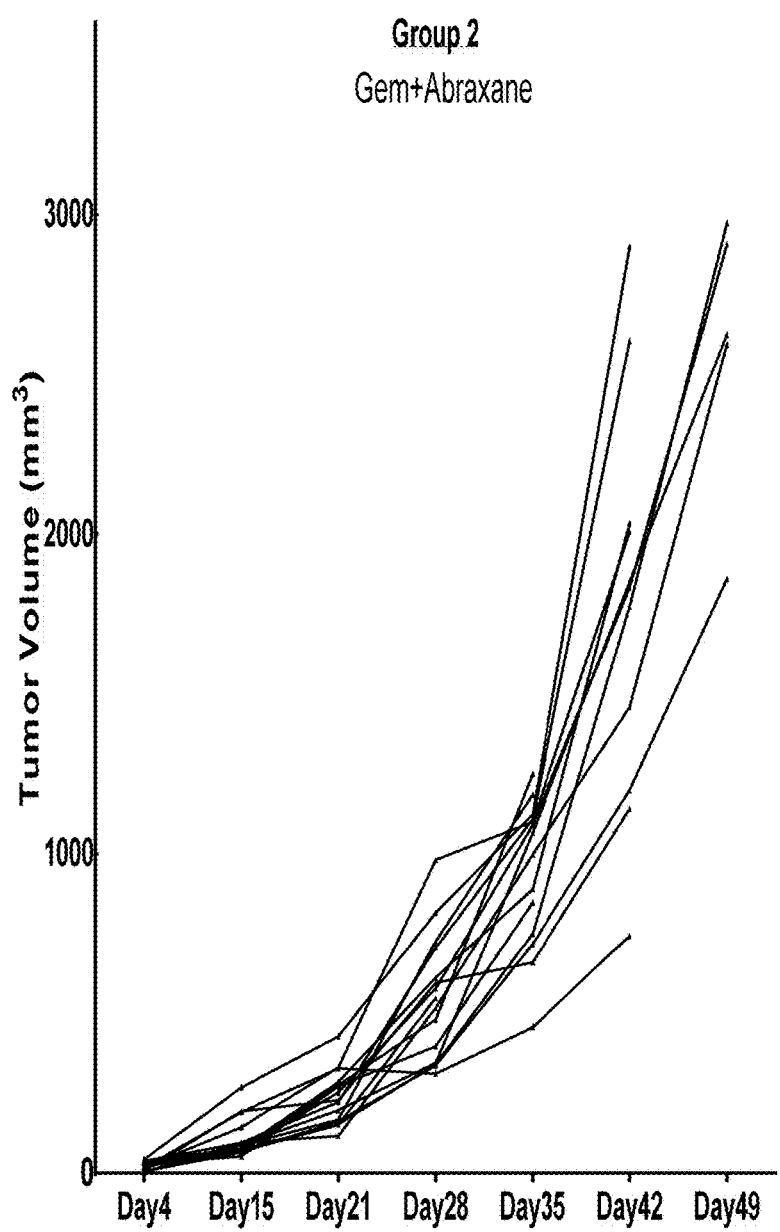
Figure 3C:
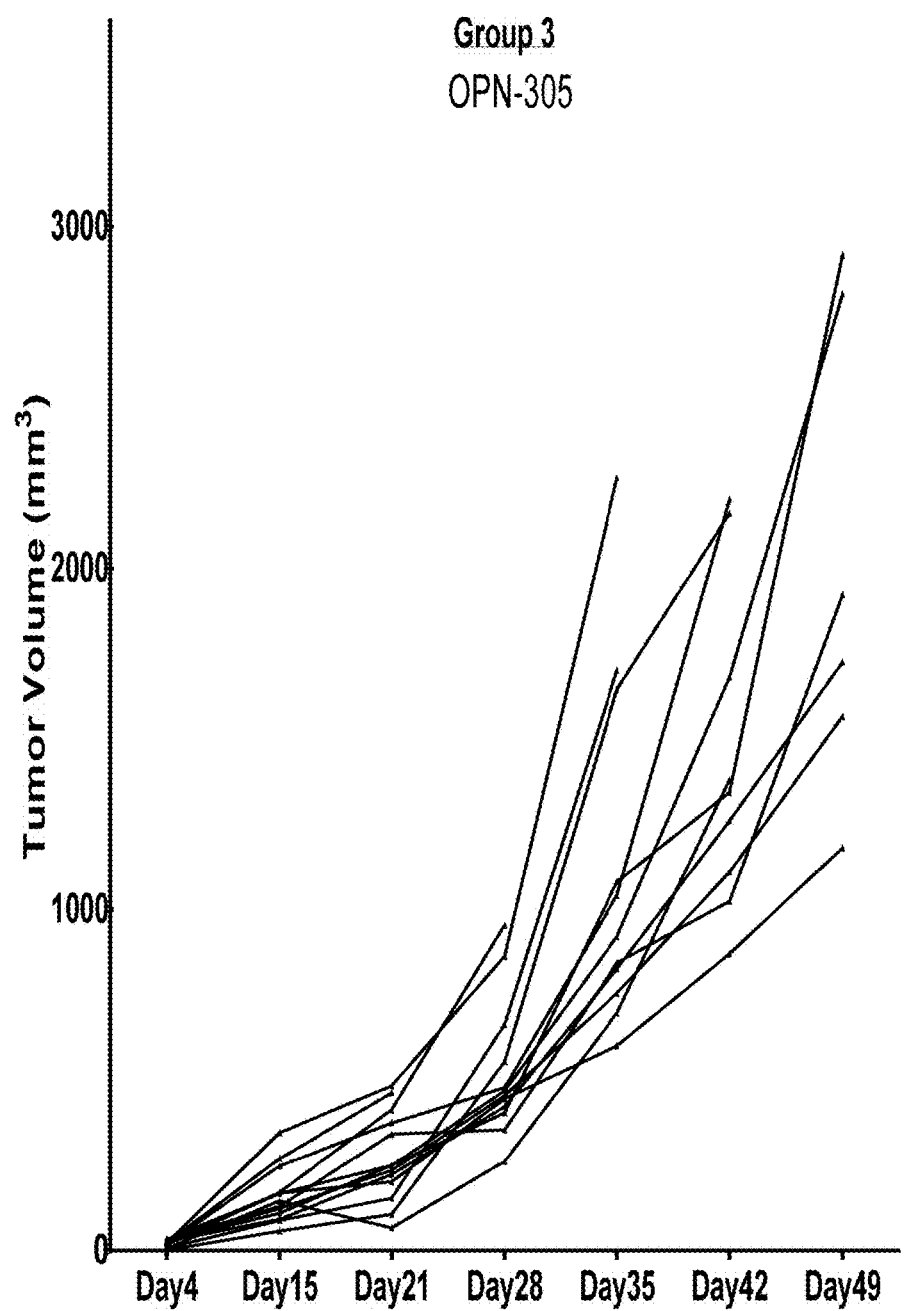
Figure 3D:
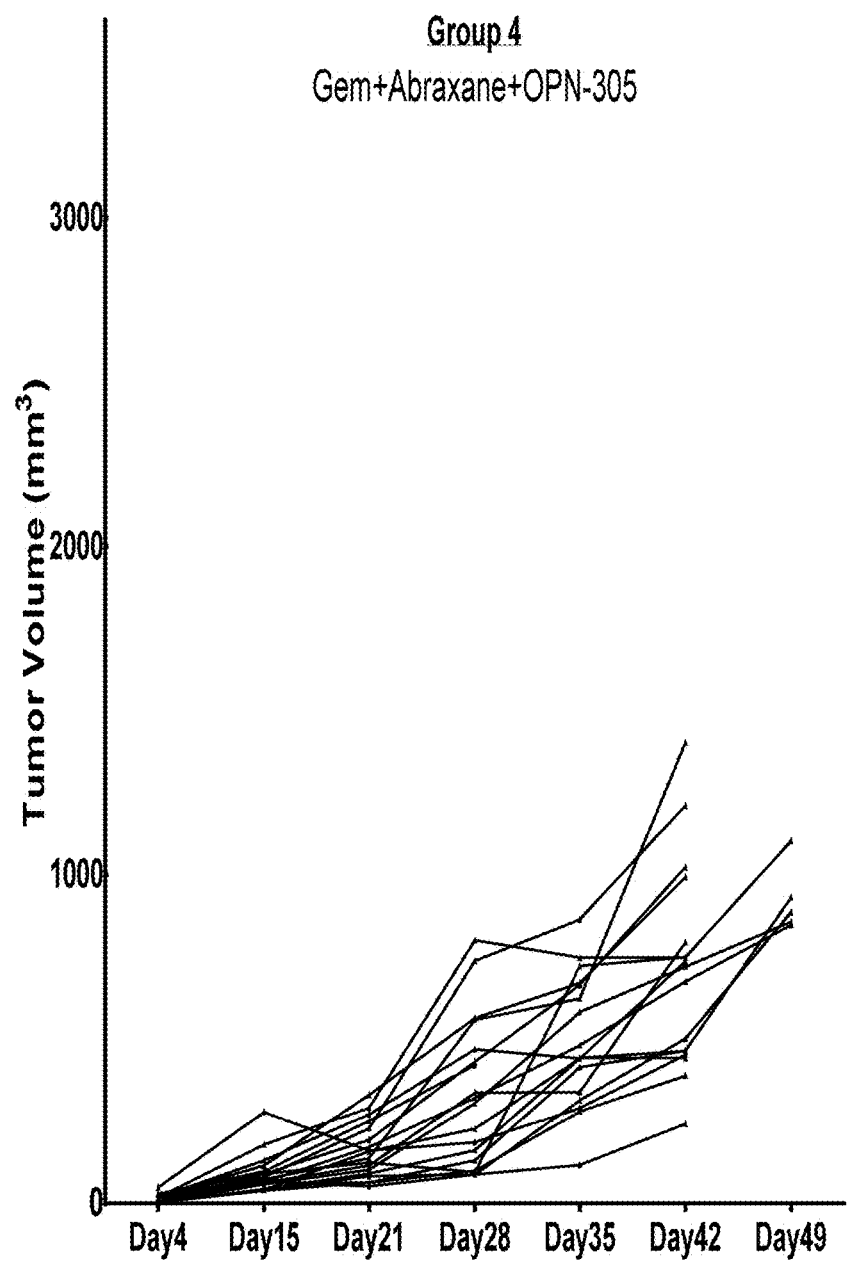
Figure 3E:
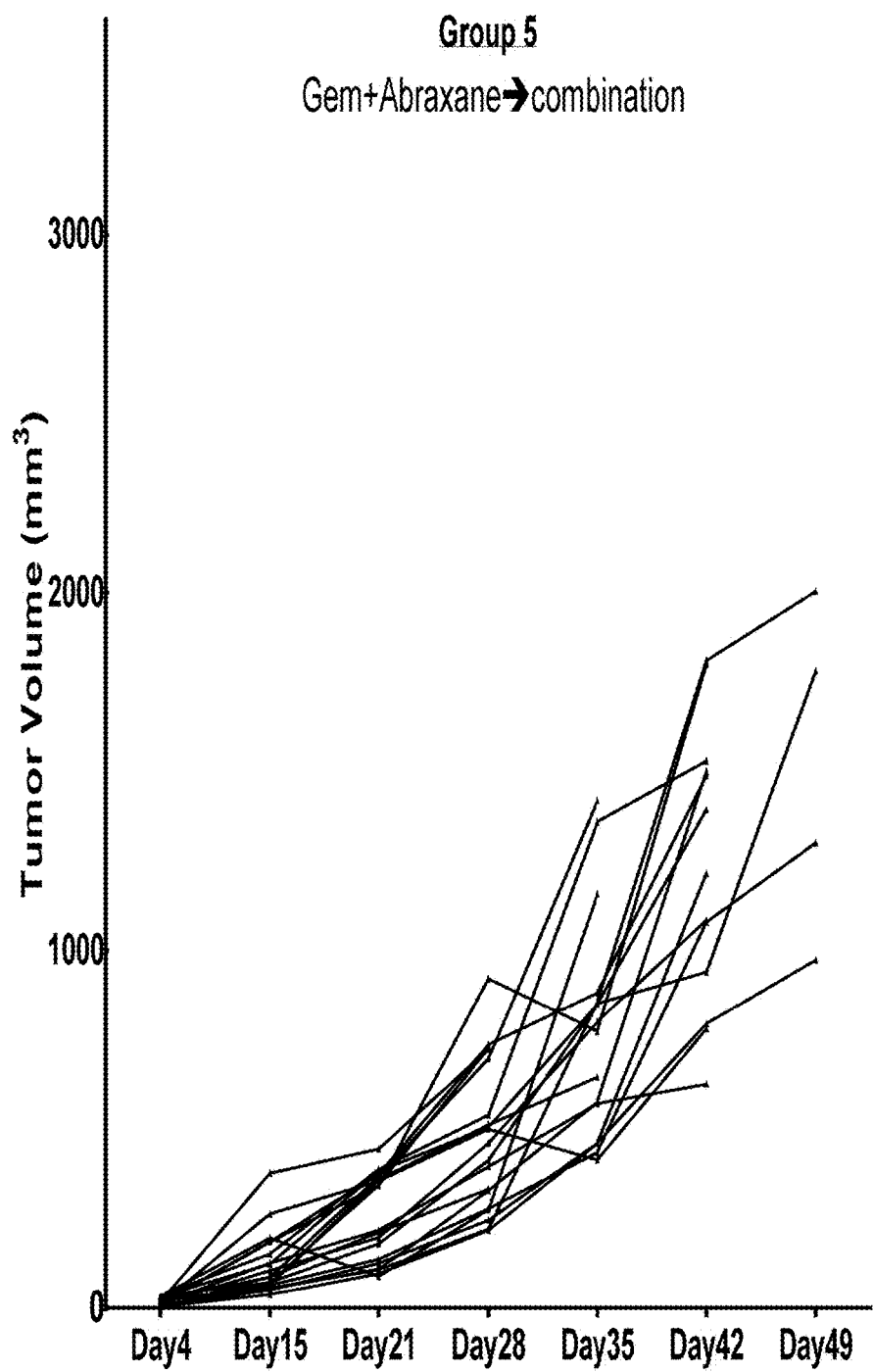
Figure 3F:
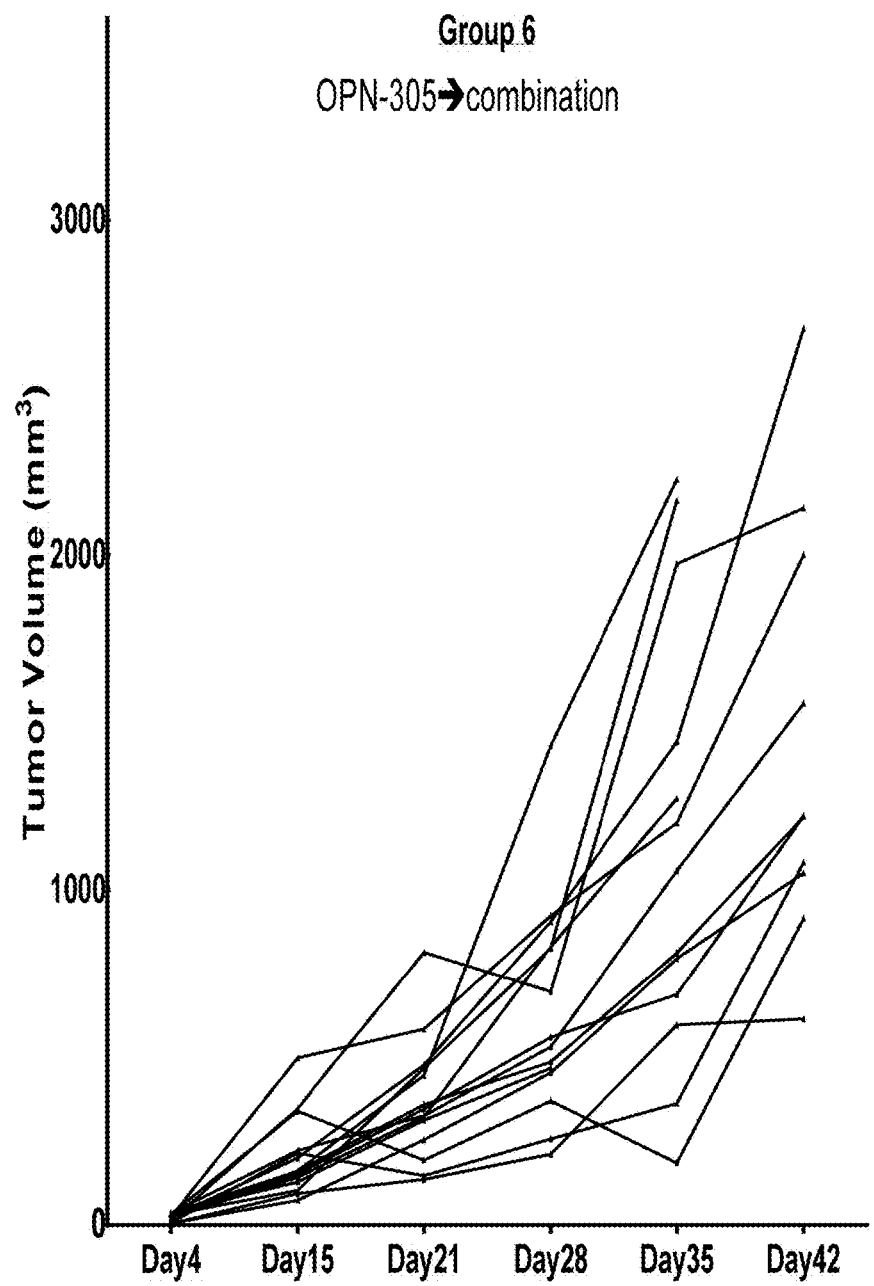
Figure 4A:
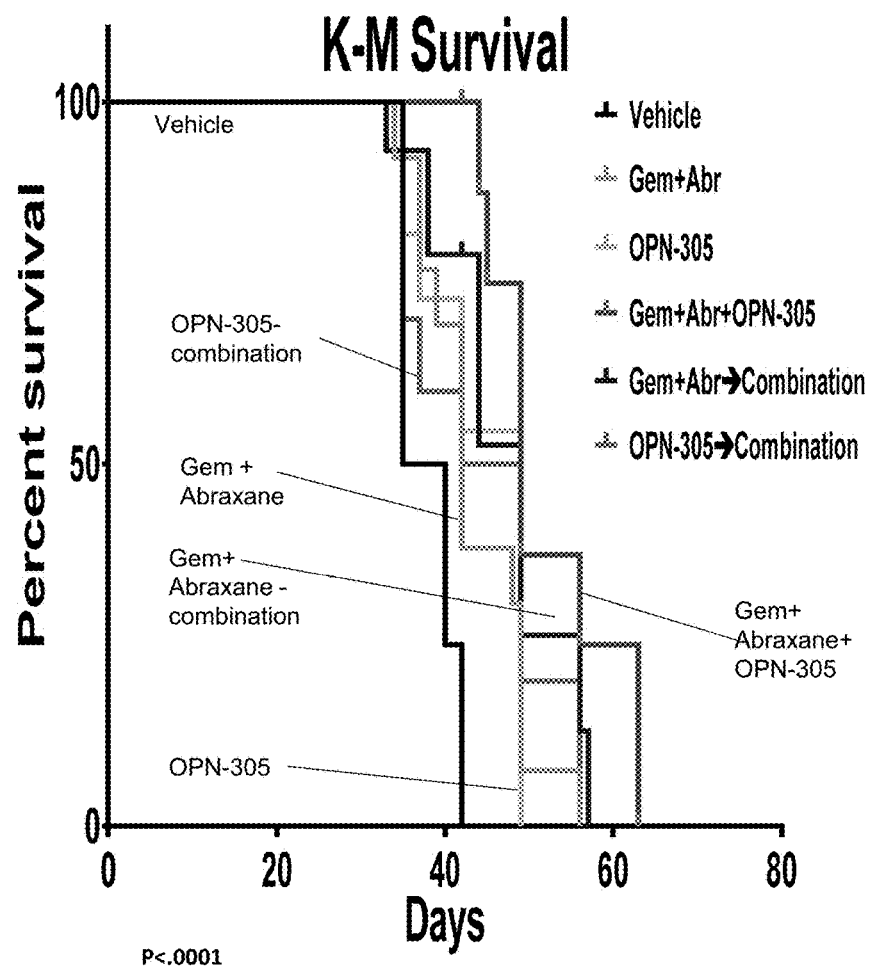
FIG. 4(a) shows percentage survival of mice treated in different treatment groups.
Figure 5A:
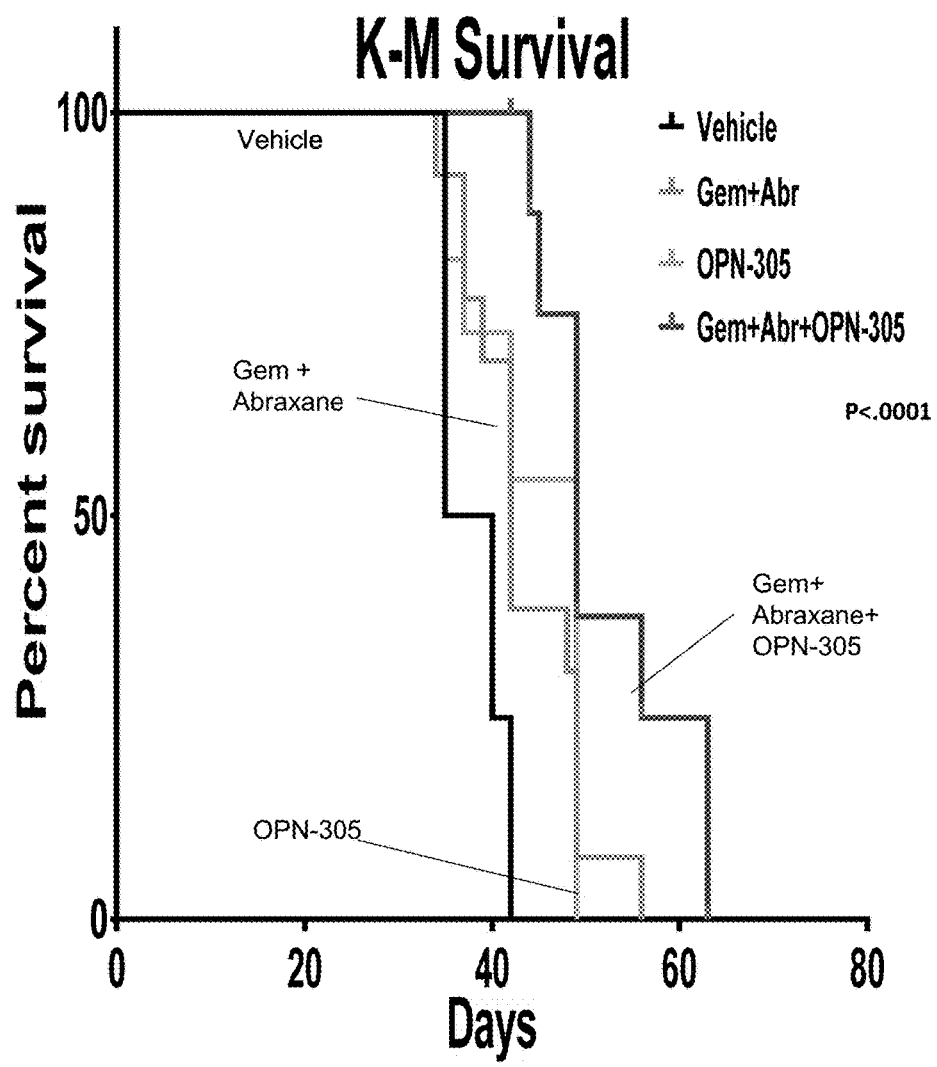
FIG. 5(a) shows percentage survival of mice treated in different treatment groups.
Figure 6A:
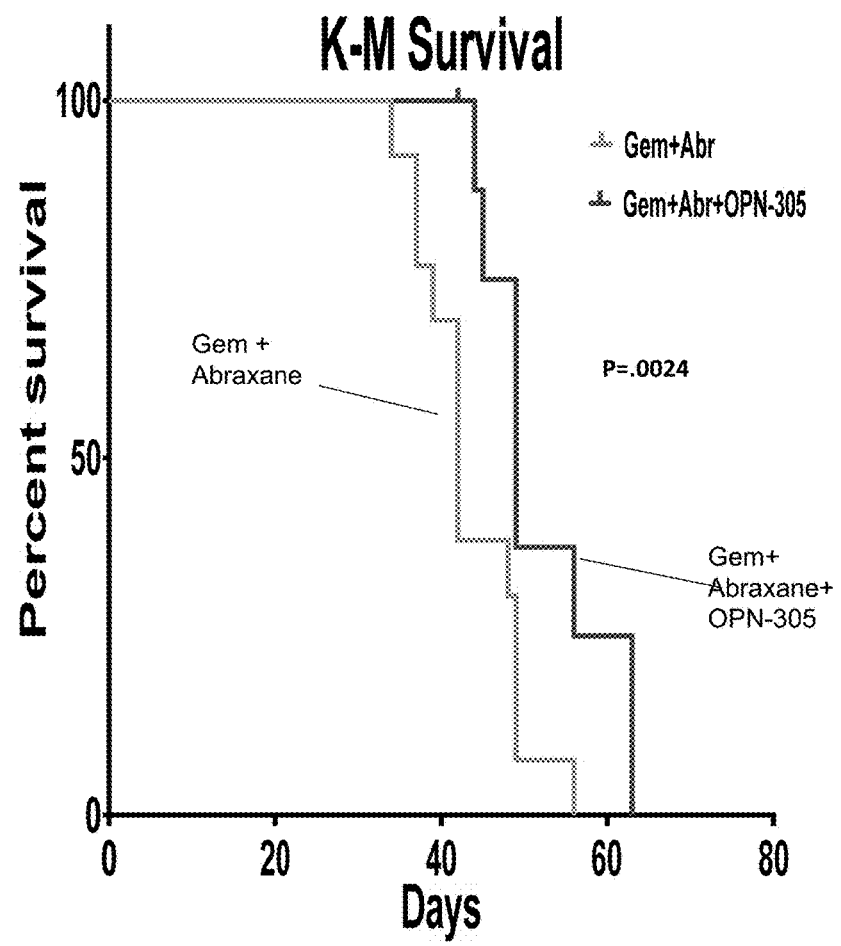
FIG. 6(a) shows percentage survival of mice treated in different treatment groups.

Results of the experiments carried out are shown in FIGS. 1-6. Treatment with OPN-305 at the induction of tumours reduced tumour volume to a greater extent than treatment with a combination of Gemcitabine+Abraxane (FIG. 1). Treatment with gemcitabine+abraxane+OPN-305 at the induction of tumours further improved reduction of tumour volume and reduced tumour volume to a greater extent than any other treatment regimen (FIG. 1). Tumour volume measurements taken during the treatment period show that the gem+Abrax+OPN-305 treatment group showed improvement over the gem+Abrax group as early as 28 days after treatment and this was maintained for up to 42 days (FIG. 2). Average tumour volume data after Day 42 becomes less representative due to reduction in mice numbers from death. Graphs showing comparisons of survival between different treatment groups are shown in FIGS. 4-6. These show the improved survival of the OPN-305 group over the gemcitabine+abraxane group and that the survival of the gem+Abrax+OPN-305 group was significantly better than the other groups.

This data shows that treatment of mice induced to have pancreatic cancer with OPN-305 had improved survival over treatment with the combination of gemcitabine+abraxane and that treatment of mice with the combination of gemcitabine+abraxane+OPN-305 had further improved survival over treatment with either antibody alone or the combination of gemcitabine+abraxane.

EXAMPLE 2—Therapeutic Efficacy of TLR2 Targeting in Pancreatic Cancer in Preclinical Setting—KPC Model To directly address questions concerning the requirements for tumour progression, Hingorani et al. (Cancer Cell. 2005 May; 7(5): 469-83) targeted endogenous expression of Trp53R172H, an ortholog of one of the most common TP53 mutations in human PDA, to progenitor cells of the mouse pancreas. The authors found that physiologic expression of Trp53R172H, in the context of concomitant endogenous KrasG12D expression, promulgates the development of invasive and widely metastatic pancreatic ductal adenocarcinoma that recapitulates the principal clinical, histopathological, and genomic features of the cognate human condition. These mice are termed KPC mice. KPC mice develop a spectrum of premalignant lesions called Pancreatic Intraepithelial Neoplasia (PanINs) that ultimately progresses to overt carcinoma with 100% penetrance. The tumours generally have a moderately differentiated ductal morphology with extensive stromal desmoplasia, similar to the most common morphology observed in humans. Metastases are observed in 80% of KPC mice, primarily in the liver and lungs, the same sites most commonly observed in humans. The tumours exhibit numerous immunohistochemical markers of PDA and harbour complex genomic rearrangements indicative of genomic instability. Furthermore, KPC mice develop the co-morbidities associated with human PDA such as cachexia, jaundice and ascites. Finally, pancreatic tumours in KPC mice are predominantly resistant to chemotherapy, with only 12% of tumours demonstrating a change in growth kinetics after treatment with gemcitabine (Science. 2009 Jun. 12; 324(5933):1457-61).

A genetic model of pancreatic cancer is used that accurately recapitulates all stages of the human disease and there is a prominent immunosuppressive leukocyte infiltrate, even in pre-invasive lesions, of tumour associated macrophages (TAM), MDSC and Tregs, that persists through invasive cancer. The model is generated by targeting endogenous KrasG12D to progenitor cells of the mouse pancreas and recapitulating a full spectrum of pancreatic intraepithelial neoplasias (PanINs) (KC mice=LSL-KRASG12D/+, PDX-1-Cre) that progress at low frequency to invasive and metastatic tumours. At 10 weeks of age, mice in which endogenous KrasG12D is targeted to pancreatic progenitor cells have a spectrum of pre-invasive lesions (PanIN 1, further progression to PanIN 2a,b and 3) with a marked inflammatory component that includes innate and adaptive immune cells. When a point mutant allele of the Li-Fraumeni human ortholog Trp53R172H is concomitantly targeted to the pancreas, all mice develop invasive and metastatic disease (KPC mice=LSL-KrasG12D/+; LSL-Trp53R172H/+; Pdx-1-Cre). Cell lines, KPC cell lines (kras-p53-cancer cell lines derived from LSL-KrasG12D/+; LSL-Trp53R172H/+; Pdx-1-Cre tumour bearing mice) are generated and grown orthotopically in C57Bl/6 mice.

Objectives

To study the therapeutic potential of TLR2 antagonists with and without the combination of conventional chemotherapy in a genetic model of pancreatic cancer looking at:
1. tumour development, progression and survival;
2. leukocyte infiltrate, function and phenotype;
3. angiogenic switch and vascular editing; and
4. interaction between innate and adaptive immunity in the microenvironment.

Research Outline

Research is carried out using the genetic model of pancreatic cancer (LSL-KrasG12D/+; LSL-Trp53R172H/+).

The group size is calculated on the basis to obtain a 90% chance of detecting a statistically significant difference given a 50% response (i.e. 50% tumour growth/incidence or metastasis or histological score, or a 50% difference in macrophage recruitment, difference in macrophage phenotype).

For the following experiments, up to n=6 LSL-KrasG12D/+; LSL-Trp53R172H/+; Pdx-1-Cre female mice/group are recruited.

In addition to the combination with the standard of care, gemcitabine, TLR2 nAb with a combinational chemotherapy regime of gemcitabine and abraxane is tested to check for enhancement of an anti-tumour microenvironment at a later time point.

Method

KPC pancreatic tumours are predominantly resistant to gemcitabine. Mice are inoculated with a tumour of 5-10 mm$^3$, randomised into their treatment groups when the tumour is approximately 25 mm$^3$ and treatment commences when the tumours are approximately 100 mm$^3$. Mice are enrolled prior to treatment with either saline or gemcitabine (100 mg/kg, Q3dx4, i.p.) with and without TLR2 nAb, or TLR2 nAb alone. At the end of treatment, mice are sacrificed and samples collected for analysis. Tumours are analysed by IHC for markers of progression, proliferation, leukocyte infiltrate, angiogenesis and stromal reaction. To assess the functional vasculature, biotin-conjugated Lycopersicon esculentum lectin is injected i.v prior to euthanasia. Masson's trichrome and α-smooth muscle actin are used to visualize the extracellular matrix and stromal architecture.

Detailed Experimental Outline:
Treatment protocol 1 (24 KPC mice):
1. untreated
2. Gemcitabine (100 mg/kg, every $3^{rd}$ day for four cycles (Q3dx4), i.p.)
3. Gemcitabine (100 mg/kg, Q3dx4, i.p.)+once weekly TLR2 nAb (1 mg/kg)
4. OPN301 alone once weekly
5. Isotype Alone once weekly
6. Gemcitabine+Isotype Treatment protocol 2 (KPC mice):
Gemcitabine 100 mg/kg every $3^{rd}$ day for four cycles (Q3dx4) i.p
OPN305 10 mg/kg weekly i.v. (until death)
Abraxane 10 mg/kg Daily for five days, i.v. (Q1dx5)
OPN305 F(ab')2 TBD
OPN301+Gem
OPN305+Gem
OPN305
OPN305 Fab2+Gem
Untreated
Abraxane
Abraxane+305

Mice are treated i.v. with 10 mg/kg of antibody weekly starting on the first day of gemcitabine therapy. Gemcitabine therapy typically lasts 9 days and the mean survival is 25 days. In order to plan for the amount of antibody to reserve for this study, it is planned to administer OPN301 until day 63 (9 weeks of treatment).

Amount of antibody required (mice assumed to be 20-25 g)

| | |
|---|---|
| (6 mice) × (9 treatments) × (25 µg/mouse) × (2 groups) | 2700 µg |
| Wastage of 25% | 675 µg |
| Total | 3375 µg |

Tumours are analysed by FACS to quantify leukocyte infiltration using cell surface markers CD8, CD4, NK1.1, CD11b, CD11c, Gr-1, F4/80, CD124 and B220, and markers of T cell and APC activation including T cell: CD69, CD25, CD44, CD62L and CD124; and APC: CD80/86, MHC II, CD206, CD124, CD69, CD200 and Dectin 1. Intracellular cytokine staining for IFNγ, IL-10 and IL-4 is performed on CD4+ and CD8+ TIL and draining lymph node (LN) T cell populations both directly and after magnetic bead separation and ex vivo culture in the presence of PMA and ionomycin for 4 days. Tumour tissue is collected and processed for routine histological analysis and IHC staining for leukocyte subsets. Plasma samples collected from the experiments are screened for cytokine and growth factors (including TNFα, IL-1β, IL-1α, IFNγ, IL-10, IL-4, IL-5, IL-12 (p70), IL-23 (p23), IFNγ, IL-6, CSF-1, TGFβ1, CXCL1, CXCL12 and VEGF) by multiplex assay using the IoC Meso Scale Discovery (MSD) platform. In addition peripheral blood samples are collected and the phenotype and Ly-6C+ and Ly-6Clo circulating monocyte subsets characterised. Plasma samples are measured for circulating levels of OPN301.

A large panel of qPCR primers for analysis of TAM and tDC phenotype is accumulated and validated (including inducible enzymes: Arginase 1, NOS2, COX2 and IDO; receptors: MR, RANK, CD40, CXCR4, CCR7; cytokines: IL-12p40, IL-12p35, IFNβ, TNFα, IL-1β, IL-1α and IL-10; chemokines: CCL2, CXCL12, CCL17, CXCL1, CXCL10 and CXCL9; and signalling proteins: PAI2, SOCS1/3, IkBa, A20 and BCL3). T cells are also characterised by Gata-3, ROR-γT, T-BET and FoxP3. Tumour associated macrophages are recruited into tumours as monocytes from the bloodstream by chemotactic cytokines and growth factors such as CCL2 (MCP-1), M-CSF (CSF-1), vascular endothelial growth factor (VEGF), angiopoietin-2 and CXCL12 (SDF1). TAM acquire a specific phenotype that is oriented toward tumour growth, angiogenesis and immune-suppression and many studies have shown a positive correlation between the number of TAM and poor prognosis in human tumours. There is also increasing evidence that TAM contribute to suppression of anti-tumour immune responses, in particular the M2-phenotype of TAM is associated with increased expression of arginase 1 and indoleamine 2,3-dioxygenase (IDO) that inhibit T-cell proliferation, as well as immunosuppressive cytokines IL-10 and TGFβ. Blockade of TAM recruitment, for example by the genetic deletion of CSF-1, blocks tumor growth, angiogenesis, and metastasis in experimental models of cancer. Tolerant DCs (tDCs) block DC activation. The increased ratio of tolerant DCs/activated DCs promotes formation of regulatory T-cells (Tregs) and inhibits effector T-cells. Leukocytes commonly infiltrate solid tumours, and have been implicated in the mechanism of spontaneous regression in some cancers.

Tumour apoptosis and proliferation are assessed by injection of the thymidine analog 5-bromo-2'-deoxyuridine (BrdU) followed by Caspase 3 staining to assess the proliferation index. 250 µl of BrdU at 50 µg/g of total body weight is injected i.p. 90 minutes after BrdU injection, mice are sacrificed and each pancreas is processed and stained. Histological analysis of pancreases is carried out by standard procedures. Specimens are harvested from time-matched animals and fixed in 4% v/v buffered formalin overnight at 4° C. The following day, the organs are progressively dehydrated in gradient alcohols (30 minutes at room temperature in 30, 50 and 70% v/v ethanol). Tissues are embedded in paraffin and sections are cut with a microtome (5 µm thickness) and prepared by the Barts Cancer Institute pathology department. The BrdU antibody from the BrdU labelling and detection kit is used (Roche—11299964001) and the peroxidase activity is visualised using SIGMAFast™ 3,3'-diaminobenzidine (DAB) with metal enhancer at a final concentration of 0.5 mg/ml DAB, 0.2 mg/ml cobalt chloride, 0.3 mg/ml urea hydrogen peroxide, 0.05 M Tris buffer and 0.15 M sodium chloride (Sigma-Aldrich—D0426).

Sections are stained using a standard streptavidin-peroxidase complex technique and the following steps are carried out at room temperature using immunoboxes for washes. Sections are deparaffinised and rehydrated. To improve the exposure of antigen sites on the sections, an antigen retrieval step is usually necessary, which is specific for each primary antibody used. The heat-mediated method is used, which involves immersing the sections in antigen citric acid based unmasking solution (Vector Labs—H-3300) and heating for 9 minutes in a microwave. Sections are allowed to cool down at room temperature for at least 20 minutes and washed three times for 3 minutes each wash in PBS. Sections are circled with ImmEdge™ hydrophobic barrier pen (Vector Labs—H4000) and blocked for non-specific binding with PBS/BSA/Goat serum for 1 hour at room temperature in a humidified chamber. Sections are incubated in primary antibody or isotype control diluted in blocking solution overnight at 4° C. in a humidified chamber. The following day, the sections are again washed three times for 3 minutes each wash in PBS and subsequently the biotinylated secondary antibody is applied and the sections are incubated for 45 minutes at room temperature in a humidified chamber. Sections are again washed three times for 3 minutes each wash in PBS and the endogenous peroxidase activity is quenched by incubating the sections in 0.3% v/v $H_2O_2$ diluted in 100% v/v methanol for 20 minutes at room temperature. The sections are then washed three times for 3 minutes each wash in PBS and avidin biotinylated peroxidase complex (Vector Labs—Vectastain Elite ABC Kit—PK-6100) is added onto the sections and incubated for 30 minutes at room temperature in a humidified chamber. The sections are once again washed three times for 3 minutes each wash in PBS and the peroxidase activity is visualised using SIGMAFast™ 3,3'-diaminobenzidine (DAB) at a final concentration of 0.7 mg/ml DAB, 0.67 mg/ml urea hydrogen peroxide and 0.06 M Tris buffer (Sigma-Aldrich—D4418). DAB solution is applied on each section for at least 3 minutes or until a brown colour develops. Subsequently, sections are briefly washed in water to stop DAB development and counterstained by dipping in haematoxylin solution (Sigma-Aldrich—GSH316) for 30 seconds, washed in water and dipped 10 times in ammonium hydroxide (44.4 mM in water) for acid differentiation. Sections are dehydrated by dipping them 20 times in isobutanol (Fisher Scientific—B/5100/PB17) and incubated again in fresh isobutanol for 4 minutes and then twice in xylene for 5 minutes. Slides are air-dried and mounted with DPX mounting medium (Fisher Scientific—D/5319/05). Cleaved Caspase 3—cell signalling, Cat No 9664. rabbit IgG, 1:200; Isotype control rabbit IgG, BD Bioscience 550875, 1:200.

Enriched blood samples are stained for various markers prior to flow cytometric analysis or flow sorting. For analysis and sorting based on endogenous YFP and surface markers, primary antibodies (1:100) and secondary antibodies (1:50) are incubated with cells in 10% FCS/DMEM/F12 for 20 minutes at 4° C. Primary pancreas samples and PanIn and PDAC cell lines from the reporter mice are used as positive controls. Isotype controls are also run.

EXAMPLE 2(a)—Analysis of TLR2 Inhibition in Combination with Gemcitabine

Mice are inoculated with a tumour of 5-10 mm³, randomised into their treatment groups when the tumour is approximately 25 mm³ and treatment commences when the tumours are approximately 100 mm³. Gemcitabine is the standard first line therapy for pancreatic cancer. However, many patients are resistant to this treatment and the increase in overall survival (OS) is modest. This is also the case in KPC mice. In order to test the efficacy of anti-TLR2 in pancreatic cancer, mice are treated with gemcitabine alone, OPN301 (or OPN305) alone, as well as the two treatments in combination. In studies where OPN301 is used, an IgG1 isotype is used as a control. This is not possible in studies where OPN305 is used as no corresponding isotype is available.

EXAMPLE 2(b)—Analysis of Effect of OPN301 and Gemcitabine Treatment on Metastatic Index The "metastatic index" is calculated by determining if tumours are found in the lung, liver, peritoneal cavity, lymph nodes and if there is bile duct obstruction. A value of 1 is recorded if a tumour(s) is present, and 0 if absent. This is averaged for each group. Liver metastasis is assessed by sectioning through the liver and counting metastasis on at least 10 slides per animals 100 μm apart.

Tumour proliferation is assessed based on % BrdU+ cells following injection of mice with BrdU and based on caspase 3 staining. Apoptosis is assessed by cleaved caspase 3 and proliferation is assessed by Ki67 expression. The calculated proliferation index (a ratio of caspase 3 expression and ki67 expression) provides an indication of the tumour turnover. As tumour cells express TLR2 in this model, the TLR2 antagonist may increase sensitivity to gemcitabine, or, in addition to the chemotherapeutic effect, the TLR2 antagonist may provide an additional immunostimulatory effect which increases the overall immune response.

The number of circulating YFP+ cells per ml blood is calculated following treatment of mice with either saline or gemcitabine (100 mg/kg, Q3dx4, i.p.) with and without TLR2 nAb OPN-301 (T2.5). KPC mice are used with a YFP label on the pancreatic tumour cells. This allows cells to be tracked in vivo by tracking YFP expression in the blood and distal organs. YFP+ cells in the blood represent "early" metastatic cells. IF is carried out using a TLR2 antibody from Santa Cruz.

EXAMPLE 2(c)—Analysis of Effect of OPN301 and Gemcitabine Therapy on the Immune-Cellular Composition of Tumours The tumour mass usually consists of tumour cells and infiltrating immune cells. Tumours are analysed by FACS to quantify leukocyte infiltration using cell surface markers and markers of T cell and APC activation. Cytokines, growth factors, and the transcription factors hes1 and hey1 are also analysed. qPCR for F4/80, CD8a, CCR1, CCR3, NK1.1, CD208, B220 and CXCR1 is used as an initial crude read-out to determine differences on total PDAC RNA for differential recruitment of leukocytes. Inflammatory cytokines have been described as tumour drivers in the KPC mouse model. Assessment of inflammatory cytokines is a possibility of assessing infiltrating leukocytes and their production of these cytokines. Hes1 and hey1 are markers for PDAC progression and are used to define the impact of treatment on disease progression. In order to eradicate a tumour, an effective immune response is required and cells typically involved in tumour clearance are NK cells, Th1 CD4+ cells and CD8+ CTLs.

EXAMPLE 2(d)—Analysis of Effect of OPN305 and Gemcitabine Therapy on Duct Morphology and TLR2 Expression Epithelial cadherin (Ecad) is a Ca(2+)-dependent cell-cell adhesion molecule that connects cells via homotypic interactions. Its function is critical in the induction and maintenance of cell polarity and differentiation, and its loss of downregulation is associated with an invasive and poorly differentiated phenotype in colon and other tumours. Retention of Ecad is thus associated with retention of ductal morphology.

EXAMPLE 2(e)—Analysis of Effect of Abraxane on Gemcitabine and OPN305 Therapy

Abraxane is added to OPN305 alone, gemcitabine alone or all three agents are combined.

EXAMPLE 2(f)—Analysis of Effect of OPN305 on the Efficacy of Second Line Pancreatic Cancer Therapy FOLFIRINOX is a combination of four chemotherapeutic agents—5-FU, leucovorin, irinotecan and oxaliplatin. Because of the increased number of drugs administered at once, there tends to be higher toxicity in humans. The combination of the four drugs tends to be lethal in mice and with this in mind two drugs (5-FU and oxaliplatin) are chosen to represent second line therapy for use in combination with OPN305. In a clinical trial comparing gemcitabine and FOLFIRINOX, the median OS, median progression-free survival, objective response rate and adverse effects are compared between the FOLFIRINOX group and the gemcitabine group.

Using the same mouse model as described above mice are either untreated, treated with 5-FU (5 mg/kg)/Oxaliplatin (6 mg/kg) or treated with 5-FU/Oxaliplatin and OPN-305 (10 mg/kg) and overall survival is assessed and compared with overall survival for chemotherapy treatments alone and controls

EXAMPLE 2(e)—Efficacious Chemotherapeutic Agents Increase TLR2 Expression

Agents, including gemcitabine, the combination of 5-FU & oxaliplatin and abraxane are tested for their ability to increase myeloid infiltrate, which is known to correlate with increased TLR2 expression (Arslan et al. 2010, Harokopakis & Hajishengallis 2005, Angel et al. 2007, Bryan et al. 2005 and Zhou et al. 2008).

EXAMPLE 3—Analysis of the TLR2 Epitope Bound by OPN-305

International Patent Application No. PCT/EP2013/056824 describes the use of electron microscopy to determine the TLR2 epitope bound by OPN-305. As OPN-305 and OPN-301 share the same epitope, this is also the epitope bound by OPN-301 (T2.5). Binding of this epitope by an antagonistic antibody or an antigen binding fragment thereof results in antagonism of TLR2 biological function, in particular activation and signalling. In particular, binding by the antibody or antigen binding fragment thereof serves to inhibit activation of the TLR2 receptor, irrespective of whether a TLR2 heterodimer is formed with another TLR, such as TLR1, TLR6, TLR4 or TLR10. The OPN-301 and OPN-305 antibodies which bind to this epitope are effective in the treatment of pancreatic cancer.

Visualization of TLR2/Fab by EM

A histidin-tagged extracellular domain (ECD) of murine TLR2, mTLR225-587-His, was prepared as described in International Patent Application No. PCT/EP2013/056824—this is termed as simply TLR2 from here on. A TLR2/OPN-305 Fab complex was formed and purified as described in International Patent Application No. PCT/EP2013/056824 and used in negative stain EM experiments. In order to perform a reconstruction of a 3D density map numerous steps are required. First it is necessary to collect a large stack of particles with molecules in many different orientations. In total 5174 individual particles were picked from hundreds of EM images using the sparx engine. Mathematical operations were carried out with the software SPIDER to align the particles by reference-free alignment and to classify the particles into 50 classes with identical views. Then averages were computed from the classes to generate particles pictures in high contrast. The averages represent the TLR2/Fab complex in different orientations.

Reconstruction of the 3D Density Map

Figure 7:
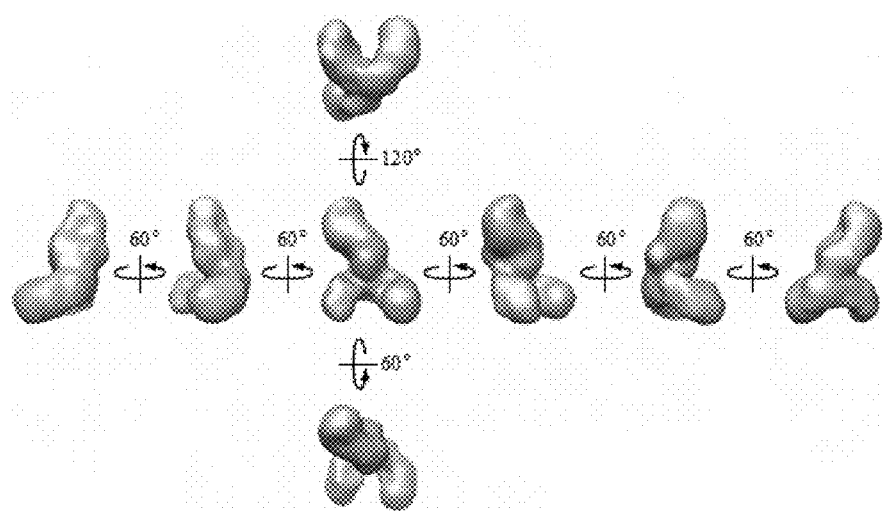
FIG. 7 shows a density map of TLR2/Fab filtered to 21.7 Å. The density map is rotated about the vertical axis in 60° steps or about 120° and 60° around the horizontal axis in reference to the centered third structure from the left, as indicated by the curved arrows. The complex structure is composed of a horseshoe-like domain and an elongated domain sitting lateral and centered on the top of the "horseshoe". Scale bar is 50 Å.

The "good" class averages were used to manually build a first 3D model in PyMOL (Schrödinger, USA) by placing the crystal structures of mTLR2 (PDB entry: 2Z81) and an IgG antibody Fab fragment (PDB entry: 2NY7) according to the particle shape seen in the averages. This model was used as a reference for single-particle reconstruction using the reference-based alignment method. First, a set of 86 2D reference projections was generated from the 3D reference model. Then, the particle stack was aligned against the 2D projections and transformations were applied according to the alignment parameters. The aligned particle images were used to create an initial 3D reconstruction, of which again 86 reference projections were generated. In total 39 iterations of back-projections were performed to refine the alignment parameters. By comparison of the generated reference-projections and the averages calculated from the particles, which were aligned to each projection, a high consistency can be observed. This demonstrates the correctness of the projections and the high quality of alignment. The back-projection method resulted in the 3D density map presented in FIG. 7.

To calculate the resolution of the 3D reconstruction, the particle data was split into two equal sets prior to the back-projection procedure, and the two resulting half-reconstruction were compared. Using the Fourier shell correlation (FSC)=0.5 criteria, a resolution of 21.7 Å was calculated from the FSC curve of the final density map. The structure of the complex is ≈130 Å×90 Å×70 Å in size and composed of a nearly planar horseshoe-like domain on which lateral and in the centre a second domain is situated, with angles of 15° and 40° tilted from the perpendicular axis on the horseshoe-like plane.

Analysis of TLR2/OPN-305 Interaction—Docking of TLR2/Fab into the Density Map

Figure 8:
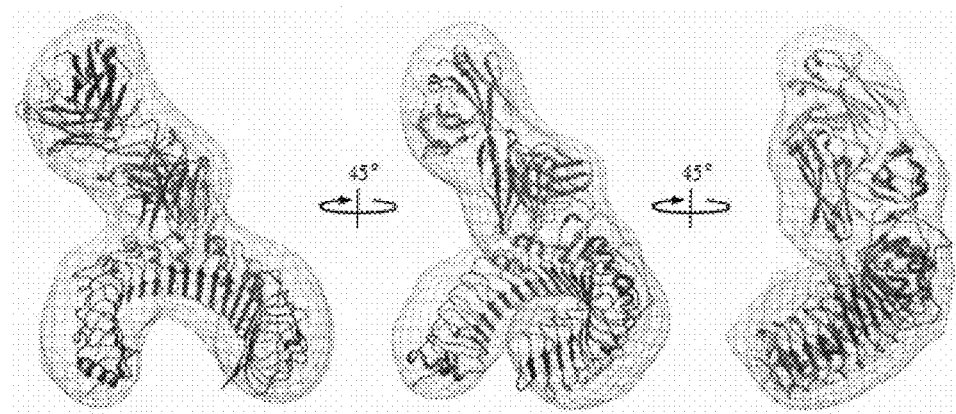
FIG. 8 shows representation of the complex molecules within the EM density map. The structure is rotated about the vertical axis in 45° steps.

To identify the interaction area between TLR2 and OPN-305 Fab, crystal structures of mTLR2 and antibody were fitted into the EM density map (FIG. 8). Like all TLRs, the ECD of mTLR2 is composed of multiple consecutive LRRs forming a solenoid structure, which is forced into a curved configuration because of closely packed β sheets on the concave surface leading to a horseshoe-like shape. The 3D reconstruction shows a similar structural feature, and the crystal structure of mTLR2 ECD (PDB entry: 2Z81) could be docked into the curved structure of the EM map (FIG. 8, bottom molecule). An antibody Fab fragment is composed of two amino acid chains, heavy and light chain, each containing one constant and one variable part. Although the crystal structure of OPN-305 is not solved, antibodies are very consistent in structure, apart from the 6 CDRs which are responsible for antigen recognition. 3D structure prediction was used to model the variable domain of OPN-305, especially to obtain a structure with correct CDR sequences and length. The crystal structure of an IgG antibody with an identical constant domain sequence to OPN-305 was then used as a framework (pdb entry: 2NY7) and its variable domain was replaced by the modelled OPN-305 variable domain. The Fab domain was placed into the EM map in the density lateral on the centre of TLR2, facing with the variable domain and its antigen binding site towards the TLR2 surface (FIG. 8).

Analysis of TLR2/OPN-305 Interaction—OPN-305 Blocks the TLR2 Dimerization Site

Figure 9:
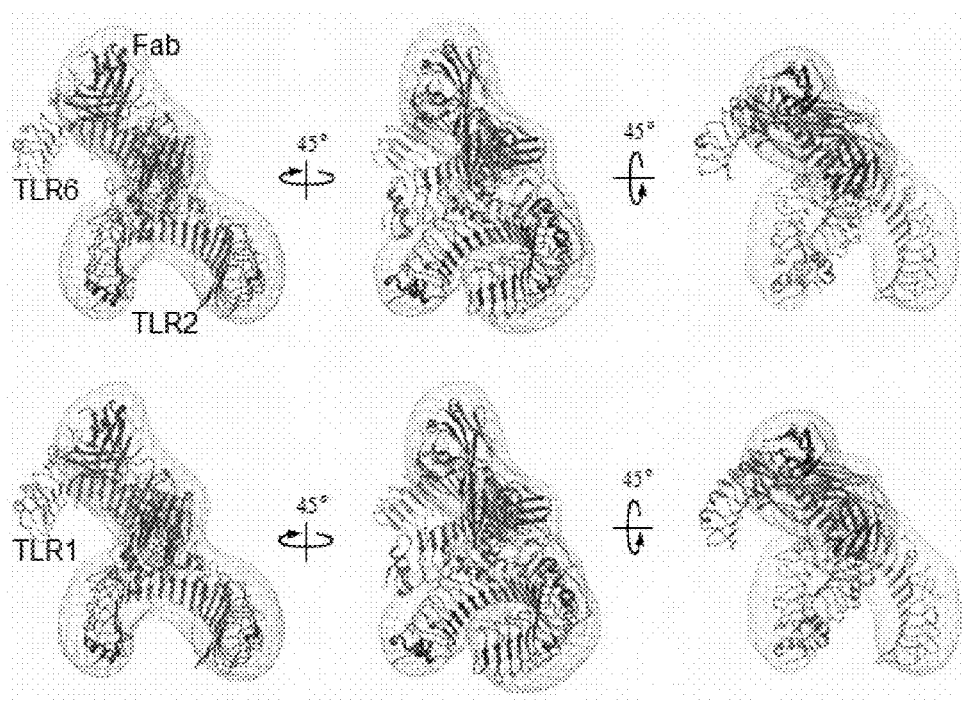
FIG. 9 shows TLR2 dimerization is blocked by OPN-305. Overlapping of TLR1 and TLR6 bound to TLR2 with OPN-305. The structure is rotated for 45° about the vertical and horizontal axis (in reference to the left structure)

After TLR2 and Fab were docked into the EM density, the structure was overlapped with the structures of TLR1 and TLR6, bound to TLR2 in the same orientation as they do in the TLR2/TLR1 and TLR2/TLR6 complexes (FIG. 9). The overlapping clearly illustrates that OPN-305 binds to TLR2 in the same region as TLR1 and TLR6. The antibody blocks the dimerization site, and thus blocks TLR1 and TLR6 of forming heterodimers with TLR2.

Analysis of the Epitope

Figure 10:
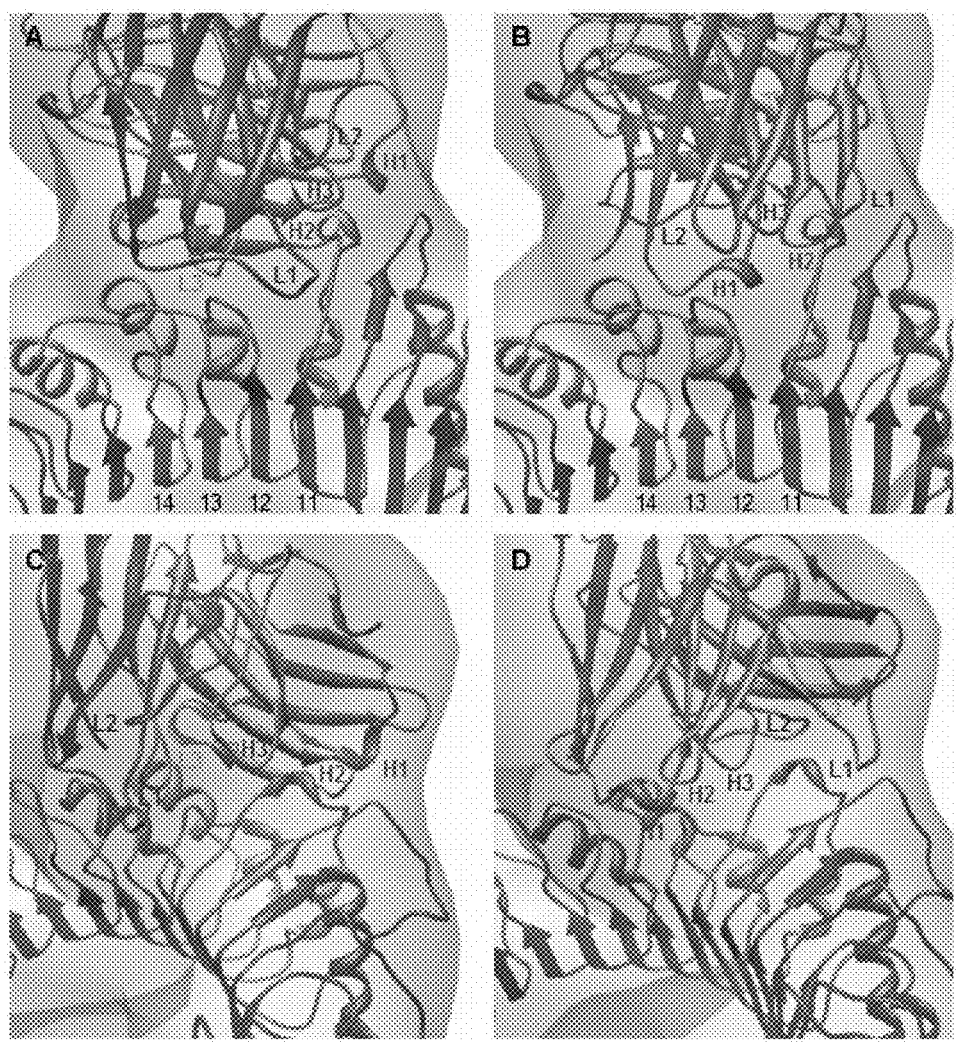
FIG. 10 shows binding of Fab to TLR2 in two theoretical orientations. Fab orientations #1 (A and C) and #2 (B and D) in two views. The six CDRs are coloured individually and are termed H1-H3 (CDRs of the heavy chain) and L1-L3 (CDRs of the light chain)

Due to the high structural homology of light and heavy chain, the quasi 2-fold symmetry of Fab allows two orientations of the domain within the density, turned at 180° to each other. The biggest differences between light and heavy chain of a Fab fragment lie in the six CDRs of the variable region, because each CDR has a different sequence and length and thus, a different conformation. Although one of the two possible orientations shows a slightly better fitting into the density, both Fab orientations were analyzed and compared to optimally predict possible surface interactions (FIG. 10). Looking at the binding interface reveals that in both possible orientations the lateral surface loops of the LRRs 11-14 are mainly involved in the interaction with the CDRs of OPN-305. Especially the exposed loop of LRR11 plays a crucial role in the recognition, as it is in close distance to at least 3 CDRs of the heavy and light chain. The optimal molecular model derived from the EM molecular surface and the molecular models of the constituent proteins clearly identifies LRR2 11-14 as the dominant site of interaction between TLR2 and the antibody Fab fragment. Despite limitations imposed by the resolution (inherent to the EM method employed) in identifying residues involved in recognition, these residues additionally need to conform to two additional criteria allowing their identity to be narrowed down: 1) their side chains must fact the antibody; and 2) the recognition residues of TLR2 should be (partly) conserved in TLR2s from different organisms with which the antibody is known to cross-react.

In total, 10 amino acids on the surface of LRRs 11-14 fulfil the first requirement outlined above, based on the structure of mTLR2 (PDB code 2Z81). They include histidine 318, proline 320, glutamine 321 and tyrosine 323 in LRR11; lysine 347 and phenylalanine 349 in LRR12; leucine 371, glutamate 375 and tyrosine 376 in LRR13; and histidine 398 in LRR14 (FIG. 10). The epitope analysis confirms the interpretation that the conserved and exposed amino acids highlighted in FIG. 11 are likely to be involved in the TLR2/OPN-305 interaction.

All documents referred to in this specification are herein incorporated by reference. Modifications and variations to the described embodiments of the inventions will be apparent to those skilled in the art, without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method for treating or preventing pancreatic cancer comprising a step of:
administering a therapeutically effective amount of a Toll-like receptor 2 (TLR2) antagonist to a subject in need thereof wherein the TLR2 antagonist is an antibody that specifically binds to TLR2, or an antigen binding fragment thereof.

2. The method as claimed in claim 1 wherein the antibody or antigen binding fragment comprises a heavy chain variable region comprising a complementarity determining region (CDR) 1 region comprising the amino acid sequence of SEQ ID NO:3, a CDR2 region comprising the amino acid sequence of SEQ ID NO:4 and a CDR3 region comprising the amino acid sequence of SEQ ID NO:5, and a light chain variable region comprising a CDR1 region comprising the amino acid sequence of SEQ ID NO:6, a CDR2 region comprising the amino acid sequence Gly-Ala-Ser and a CDR3 region comprising the amino acid sequence of SEQ ID NO:7.

3. The method as claimed in claim 2 wherein the antibody or antigen binding fragment comprises a light chain variable domain comprising the amino acid sequence of SEQ ID NO:10, or a sequence which has at least 90% amino acid sequence identity with SEQ ID NO:10, and a heavy chain variable domain comprising the amino acid sequence of SEQ ID NO:11, or a sequence which has at least 90% amino acid sequence identity with SEQ ID NO:11.

4. The method as claimed in claim 3 wherein the antibody or antigen binding fragment antagonises TLR2 function independently of binding of the antibody or antigen binding fragment to CD32.

5. The method as claimed in claim 3 wherein the method further comprises a step of administering sequentially, separately or simultaneously a therapeutically effective amount of a secondary chemotherapeutic agent.

6. The method as claimed in claim 5 wherein the secondary chemotherapeutic agent is gemcitabine.

7. The method as claimed in claim 6 wherein the method further comprises a step of administering sequentially, separately or simultaneously a therapeutically effective amount of a tertiary chemotherapeutic agent, wherein the tertiary chemotherapeutic agent is abraxane.

8. The method as claimed in claim 7 wherein the antibody or antigen binding fragment, gemcitabine and abraxane are administered simultaneously.

9. The method as claimed in claim 3 wherein the method further comprises a step of administering sequentially, separately or simultaneously a therapeutically effective amount of an immuno-oncology agent.

10. The method as claimed in claim 9 wherein the immune-oncology agent is selected from the group consisting of anti-PD-1 antibodies, anti-PD-L1 antibodies, anti-CTLA-4 antibodies, anti-CD40 antibodies and anti-CD27 antibodies.

11. The method as claimed in claim 2 wherein the antibody comprises a heavy chain comprising the amino acid sequence of SEQ ID NO:13, or a sequence which has at least 90% amino acid sequence identity to the amino acid sequence of SEQ ID NO:13, and a light chain comprising the amino acid sequence of SEQ ID NO:12, or a sequence which has at least 90% amino acid sequence identity to the amino acid sequence of SEQ ID NO:12, or an antigen binding fragment thereof.

12. The method as claimed in claim 2 wherein the antibody or antigen binding fragment comprises a heavy chain variable region comprising the amino acid sequence of SEQ ID NO:8, or a sequence which has at least 90% amino acid sequence identity to the amino acid sequence of SEQ ID NO:8, and a light chain variable region comprising the amino acid sequence of SEQ ID NO:9, or a sequence which has at least 90% amino acid sequence identity to the amino acid sequence of SEQ ID NO:9.

13. The method as claimed in claim 1 wherein the antibody or antigen binding fragment comprises a light chain variable domain comprising the amino acid sequence of SEQ ID NO:10 and a heavy chain variable domain comprising the amino acid sequence of SEQ ID NO:11.

14. The method as claimed in claim 1 wherein the antibody is a humanised version of anti-TLR2 antibody T2.5, or an antigen binding fragment thereof.

15. The method as claimed in claim 1 wherein the method further comprises a step of administering sequentially, separately or simultaneously a therapeutically effective amount of a secondary chemotherapeutic agent.

16. The method as claimed in claim 15 wherein the secondary chemotherapeutic agent is gemcitabine.

17. The method as claimed in claim 16 wherein the method further comprises a step of administering sequentially, separately or simultaneously a therapeutically effective amount of a tertiary chemotherapeutic agent, wherein the tertiary chemotherapeutic agent is abraxane.

18. The method as claimed in claim 17 wherein the antibody or antigen binding fragment, gemcitabine and abraxane are administered simultaneously.

\* \* \* \* \*

UNITED STATES PATENT AND TRADEMARK OFFICE
CERTIFICATE OF CORRECTION

PATENT NO. : 10,047,164 B2
APPLICATION NO. : 15/244833
DATED : August 14, 2018
INVENTOR(S) : Thorsten Hagemann It is certified that error appears in the above-identified patent and that said Letters Patent is hereby corrected as shown below:

In the Claims

At Column 51, Line 28, "treating or preventing pancreatic" should be -- treating pancreatic --.

Signed and Sealed this
Thirty-first Day of December, 2019

Andrei Iancu
*Director of the United States Patent and Trademark Office*